(12) United States Patent
Akiyama

(10) Patent No.: US 9,759,676 B2
(45) Date of Patent: Sep. 12, 2017

(54) GAS SENSOR ARRAY, GAS ANALYSIS METHOD, AND GAS ANALYSIS SYSTEM

(71) Applicant: KAKE EDUCATIONAL INSTITUTION, Okayama-shi, Okayama (JP)

(72) Inventor: Norio Akiyama, Okayama (JP)

(73) Assignee: Kake Educational Institution, Okayama (JP)

( * ) Notice: Subject to any disclaimer, the term of this patent is extended or adjusted under 35 U.S.C. 154(b) by 147 days.

(21) Appl. No.: 14/425,560

(22) PCT Filed: Sep. 2, 2013

(86) PCT No.: PCT/JP2013/073577
§ 371 (c)(1),
(2) Date: Jul. 13, 2015

(87) PCT Pub. No.: WO2014/034935
PCT Pub. Date: Mar. 6, 2014

(65) Prior Publication Data
US 2015/0308972 A1 Oct. 29, 2015

(30) Foreign Application Priority Data

Sep. 3, 2012 (JP) ................................. 2012-193594

(51) Int. Cl.
*G01N 33/00* (2006.01)
*G01N 27/12* (2006.01)

(52) U.S. Cl.
CPC ......... *G01N 27/122* (2013.01); *G01N 27/128* (2013.01); *G01N 33/0031* (2013.01)

(58) Field of Classification Search
CPC .. G01N 27/125; G01N 27/127; G01N 27/122; G01N 27/128; G01N 27/12; G01N 33/0031
See application file for complete search history.

(56) References Cited

U.S. PATENT DOCUMENTS 4,670,400 A * 6/1987 Leenders ............... G01N 30/68
436/161
6,046,054 A 4/2000 McGeehin et al.
(Continued)

FOREIGN PATENT DOCUMENTS

JP H03-289555 A 12/1991
JP 3626485 B2 3/2005
(Continued)

OTHER PUBLICATIONS

Candeloro et al., *Journal of Vacuum Science & Technology B*, 23(6): 2784-2788 (2005).
(Continued)

*Primary Examiner* — Blake A Tankersley
(74) *Attorney, Agent, or Firm* — Leydig, Voit & Mayer, Ltd.

(57) ABSTRACT

A gas sensor array containing a gas flow path in which a gas to be analyzed flows, and a plurality of gas sensors set along the gas flowing direction of the gas flow path, wherein the gas sensors each has a constitution wherein semiconductor microcrystals that come into contact with the gas to be analyzed that flows in the above gas flow path are disposed between two electrodes.

19 Claims, 24 Drawing Sheets

(56) References Cited

U.S. PATENT DOCUMENTS

| | | | |
|---|---|---|---|
| 9,134,265 B2* | 9/2015 | Akiyama | G01N 27/125 |
| 2006/0088445 A1 | 4/2006 | Lewis et al. | |
| 2012/0266658 A1 | 10/2012 | Akiyama et al. | |

FOREIGN PATENT DOCUMENTS

| | | | |
|---|---|---|---|
| JP | 2007-078709 A | 3/2007 |
| JP | 2011-033592 A | 2/2011 |
| WO | WO 2011/055751 A1 | 5/2011 |

OTHER PUBLICATIONS

Karthigeyan et al., *Japanese Journal of Applied Physics*, 47(9): 7440-7443 (2008).
Someya et al., *Nano Letters*, 3(7): 877-881 (2003).
Japaense Patent Office, International Search Report in International Patent Application No. PCT/JP2013/073577 (Dec. 10, 2013).

\* cited by examiner (A)

(B)

(A)

(B)

(A)

(B)

(A)

(B)

(A)

(B)

(A)

(B)

(A)

(B)

(A)

(B)

(A)

(B)

(C)

(A)

(B)

GAS SENSOR ARRAY, GAS ANALYSIS METHOD, AND GAS ANALYSIS SYSTEM

TECHNICAL FIELD

The present invention relates to an economical and compact gas sensor array using semiconductor microcrystals, which is superior in gas type discrimination property and also capable of component analysis of a mixed gas, a gas analysis method and a gas analysis system.

BACKGROUND ART

In recent years, detection of gas in the environment has become increasingly important for avoidance of danger caused by noxious gas, odorless carbon monoxide gas and the like in the environment. It is also known that a specific gas is developed due to cancer present in the body, an etiology such as diabetes and the like, and the application of a gas sensor to a noncontact diagnosis using mouth cavity gas is expected. In addition, a gas sensor which is compact and light weight, low power consuming and superior in a gas type discriminating function (property to sense a particular gas component) is desired as an instrument to be mounted on a disaster robot.

Examples of the gas sensor commercially available heretofore include a PN junction type gas sensor, a metal oxide sintered gas sensor and the like. In recent years, a gas sensor using a single-walled carbon nanotube (SWCNT) (non-patent documents 1, 2), and a gas sensor using a metal oxide nanowire (non-patent document 3) have been proposed. In addition, the applicant of the present application proposed gas sensor using a selenium nanowire (SeNW) (patent document 1). However, these gas sensors are not very good at discriminating gas types (hereinafter to be also referred to as "gas type discriminating ability"). That is, it is difficult to distinguish a gas showing similar reactivity (sensitivity) with a gas sensitive material, and the gas sensor is limitatively used under conditions for a predetermined gas type to be detected.

As a method of improving gas type discriminating ability of a gas sensor, an apparatus accumulating gas sensors has been considered. For example, patent document 2 proposes a gas sensor array comprising a combination of a semiconductor gas sensor use $Cr_{(2-x)}Ti_xO_3$ (wherein $0.3 \geq x \geq 0.05$) as a gas detection element, and a semiconductor gas sensor using $Fe_{(1-x)}B_xNbO_4$ (B is a trivalent element and $1 \geq x \geq 0$), $CrNbO_4$ or $SnO_2$ as a gas detection element. Patent document 3 proposes a gas measurement substrate unit wherein a plurality of gas adsorption films having different gas adsorption properties are accumulated on a single crystal silicon substrate. In addition, patent document 4 proposes a gas sensor array using a plurality of conductive polymer films having different gas responsiveness. However, all of these have plural gas-sensitive parts formed from materials showing different gas responsiveness, and the formation steps thereof are highly complicated. Moreover, the number of gases that can be determined is limited since it depends on the number of materials used for the gas-sensitive part. In the case of the gas sensor arrays of patent documents 3, 4, gas detection requires a detection operation at a high temperature using a heater, which consumes a large amount of electric power.

For the component analysis of a mixed gas, gas chromatography is generally used, and there is no report on the component analysis of a mixed gas by a gas sensor array accumulating gas sensors as described in patent documents 2-4. A gas sensor as semiconductor gas chromatography can only distinguish gases such as hydrogen, acetylene, ethane and the like and cannot easily distinguish various organic gases. In addition, since a metal oxide semiconductor is used for semiconductor gas chromatography, oxidation heating by a heater is necessary, thus causing high power consumption. Furthermore, since such gas chromatography requires time for analysis measurement and has a bulky apparatus unsuitable for carrying, it is not suitable for environmental monitoring at the work site.

DOCUMENT LIST

Patent Documents patent document 1: WO 2011/055751
patent document 2: JP-B-3626485
patent document 3: JP-A-2011-33592
patent document 4: JP-A-2007-78709

Non-Patent Documents non-patent document 1: Takao Someya, Joshua Small, Philip Kim, Colin Nuckolls, and James T. Yardley, Nano Letters 3 (2003) pp. 877-881.
non-patent document 2: A. Karthigeyan, N. Minami, and K. Iakoubovskii, Jpn. J. Appl. Phys. 47 (2008) pp. 7440-7443.
non-patent document 3: P. Carpentiero et al. J. Vac. Sci. Technol B 23 (2005) pp. 2784.

SUMMARY OF THE INVENTION

Problems to be Solved by the Invention

The present invention has been made in view of the above-mentioned problems, and the problem thereof to be solved is provision of an economical and compact gas sensor array that can be produced easily, can operate at room temperature, and has a superior gas type discriminating ability (particularly gas type discriminating ability of organic gas), and further, provision of a gas analysis method capable of easily discriminating the gas type.

Also, it is provision of an economical and compact gas sensor array that can be produced easily, can operate at room temperature, does not require a carrier gas as in gas chromatography, and can analyze components of a mixed gas, and further, a gas analysis method capable of analyzing components of a mixed gas with ease.

Means of Solving the Problems

The present inventors have found that microcrystalline selenium obtained by crystal growth by the catalytic action of organic solvents from amorphous selenium (especially, selenium nanowire which is fibrous or needle-like hexagonal system microcrystalline selenium) has the properties of P-type semiconductor inherent to selenium, and has high reaction sensitivity to organic gas molecules (i.e., a current flows when placed under a constant voltage, and its electric resistance increases by making contact with organic gas molecules at room temperature to decrease the current), and found that semiconductor nanocrystals, such as microcrystalline selenium and the like, which are placed between two electrodes may function as a gas sensor. Then, they arranged a plurality of gas sensors using such semiconductor microcrystals along the gas flow direction of the gas flow path, and found that the type of gas can be determined by comparing time-change spectra of the current changes that occur in each of the gas sensors, as well as the component analysis of a gas mixture can also be performed, and completed the present invention.

That is, the present invention relates to

[1] a gas sensor array comprising a gas flow path in which a gas to be analyzed flows, and a plurality of gas sensors set along a gas flowing direction of the gas flow path, wherein the gas sensors each has a constitution wherein semiconductor microcrystals that come into contact with the gas to be analyzed that flows in the gas flow path are disposed between two electrodes,

[2] the gas sensor array of the above-mentioned [1], wherein the gas sensors set along the gas flowing direction of the gas flow path are each composed of a laminate wherein an accumulation layer of the semiconductor crystals is formed on a first single-electrode, a gas flow path configured on the side of the laminate to be in contact with the aforementioned accumulation layer of the semiconductor crystals, and a plurality of second electrodes provided side by side on the aforementioned accumulation layer of the semiconductor crystals, along the gas flowing direction of the gas flow path,

[3] the gas sensor array of the above-mentioned [2], wherein the laminate wherein an accumulation layer of the semiconductor crystals is formed on a first single-electrode is a band-like laminate wherein the accumulation layer of the semiconductor crystals is formed on a single electrode having a band-like flat shape, the gas flow path is configured at least on one side of the transverse direction of the band-like laminate and along the longitudinal direction of the band-like laminate, and the second electrodes are each configured such that the axis thereof is approximately orthogonal to the longitudinal direction of the band-like laminate,

[4] the sensor array of the above-mentioned [2] or [3], wherein a conducting layer is laminated on the surface of the electrode, and the semiconductor crystals are formed on the accumulation layer of the conducting layer,

[5] the sensor array of any of the above-mentioned [1]-[4], wherein the electrode has a surface made of gold or silvery,

[6] the sensor array of any of the above-mentioned [1]-[5], wherein the semiconductor microcrystal is microcrystalline selenium,

[7] the sensor array of the above-mentioned [6], wherein the microcrystalline selenium is a selenium nanowire,

[8] the sensor array of any of the above-mentioned [1]-[7], wherein the gas to be analyzed that flows in the gas flow path comes into contact with semiconductor microcrystals of plural gas sensors under a constant voltage and a delay time between different sensors in a time-change spectrum of electric current change that occurs in each gas sensor is detected,

[9] the sensor array of the above-mentioned [8], wherein the delay time is a delay time in the start of a reaction of time-change spectrum,

[10] the gas sensor array of any of the above-mentioned [1]-[7], wherein the gas to be analyzed that flows in the gas flow path comes into contact with the semiconductor microcrystals of the plural gas sensors under a constant voltage and a difference in the shape of time-change spectrum of electric current change between different sensors is detected,

[11] the gas sensor array of any of the above-mentioned [1]-[10], which is for an organic gas,

[12] a method of analyzing a gas, comprising flowing a gas to be analyzed in a gas flow path while applying a constant voltage to plural gas sensors in the gas sensor array of any of the above-mentioned [1]-[7], and specifying the gas type of the gas to be analyzed based on a delay time between different sensors in a time-change spectrum of electric current change that occurs in each gas sensor,

[13] a method of analyzing a gas, comprising flowing a gas to be analyzed in a gas flow path while applying a constant voltage to plural gas sensors in the gas sensor array of any of the above-mentioned [1]-[7], and specifying a component ratio of the gas to be analyzed based on a delay time between different sensors in a time-change spectrum of electric current change that occurs in each gas sensor,

[14] a method of analyzing a gas, comprising flowing a gas to be analyzed in a gas flow path while applying a constant voltage to plural gas sensors in the gas sensor array of any of the above-mentioned [1]-[7], and specifying a component ratio of the gas to be analyzed from comparison of a peak arrival time between different sensors in a time-change spectrum of electric current change that occurs in each gas sensor,

[15] a method of analyzing a gas, comprising flowing a gas to be analyzed in a gas flow path under plural conditions with varying flowing time of a gas to be analyzed in the gas flow path while applying a constant voltage to plural gas sensors in the gas sensor array of any of the above-mentioned [1]-[7], observing time-change spectrum of electric current change occurring in plural gas sensors under respective conditions, and specifying gas components of the gas to be analyzed, which is composed of a mixed gas, by comparison of time-change spectra obtained under the plural conditions, and

[16] a gas analysis system comprising the gas sensor array of any of the above-mentioned [1]-[7], and a calculation part for specifying a gas type, specifying a component ratio of a mixed gas or specifying a gas component of a mixed gas, based on an electric output value based on a time-change spectrum of electric current change that occurs in each gas sensor when a gas to be analyzed is flown in a gas flow path while applying a constant voltage to plural gas sensors in the gas sensor array, and comparison results with numerical values preserved in a database.

Effect of the Invention

According to the present invention, an economical and compact gas sensor array that can be produced easily, can operate at room temperature, and has a superior gas type discrimination ability (particularly gas type discriminating ability of organic gas) can be obtained.

Since the gas sensor array of the present invention is compact, can operate at room temperature, can specify gas type, can analyze mixed gas components, and can afford analysis results in a short time, environmental monitoring at the site, loading on robots, utilization in the medical field and the like can be expected.

BRIEF DESCRIPTION OF THE DRAWINGS

FIG. 1(A) is a perspective view without a cover, and FIG. 1(B) is a perspective view with a cover.

FIG. 2(A) is a cross section of the principal part of the gas sensor array shown in FIG. 1, and FIG. 2(B) is a side view of the surface where a gas introduction port of the gas sensor array shown in FIG. 1 is formed.

FIG. 7(A) shows time-change spectrum of electric current change ($I/I_0$: I is electric current value in gas reaction, $I_0$ is initial electric current value before gas reaction) in plural gas sensors when 1-propanol gas was flown in a gas flow path of the gas sensor array of the present invention, and FIG. 7(B) is an enlarged view wherein a gas introduction start time into the gas flow path in FIG. 7(A) is the horizontal axis.

FIG. 8(A) shows time-change spectrum of electric current change ($I/I_0$) in plural gas sensors when methanol gas was flown in a gas flow path of the gas sensor array of the present invention, and FIG. 8(B) is an enlarged view wherein a gas introduction start time into the gas flow path in FIG. 8(A) is the horizontal axis.

FIG. 10(A) shows time-change spectrum of electric current change ($I/I_0$) in plural gas sensors when 1-octanol gas was flown in a gas flow path of the gas sensor array of the present invention, and FIG. 10(B) is an enlarged view wherein a gas introduction start time into the gas flow path in FIG. 10(A) is the horizontal axis.

FIG. 12(A) shows time-change spectrum of electric current change ($I/I_0$) of plural gas sensors in the gas sensor array of the present invention relative to a mixed gas of acetone and toluene having a varying mixing ratio, and FIG. 12(B) shows the relationship between a delay time in the start of a reaction of the time-change spectrum, and the position of gas sensors (position of gas flowing direction of gas flow path, gas sensor (det) No.).

FIG. 13(A) shows time-change spectrum of electric current change ($I/I_0$) of plural gas sensors in the gas sensor array of the present invention relative to a mixed gas of acetone and benzene having a varying mixing ratio, and FIG. 13(B) shows the relationship between the ratio of benzene in the mixed gas, and a peak arrival time in the time-change spectrum of electric current change.

FIG. 15(A) shows time-change spectra of electric current change in the first gas sensor (det 1) and the thirteenth gas sensor (det 13), which are counted from the gas introduction port, when a mixed gas of acetone and benzene at a mixing ratio (benzene/acetone) of 0.71/0.29 is flown in the gas flow path in the gas sensor array of the present invention, and FIG. 15(B) is an enlarged view when 20 sec-70 sec passed from the start of the measurement in FIG. 15(A).

FIG. 17(A)-FIG. 17(C) show time-change spectra of electric current change in the first gas sensor (det 1), the third gas sensor (det 3) and the ninth gas sensor (det 9), which are counted from the gas introduction port, when a mixed gas of 1-butanol and 1-octanol having a varying mixing ratio is flown in the gas sensor array of the present invention.

FIG. 21(A) shows time-change spectrum of electric current change in each of the first gas sensor (det 1)—the fourth gas sensor (det 4), which are counted from the gas introduction port, when carbon dioxide gas is flown in the gas flow path in the gas sensor array of the present invention, and FIG. 21(B) is an enlarged view wherein a gas introduction start time into the gas flow path in FIG. 21(A) is the horizontal axis.

DESCRIPTION OF EMBODIMENTS

The gas sensor array of the present invention is explained below by referring to Figures.

Figure 1:
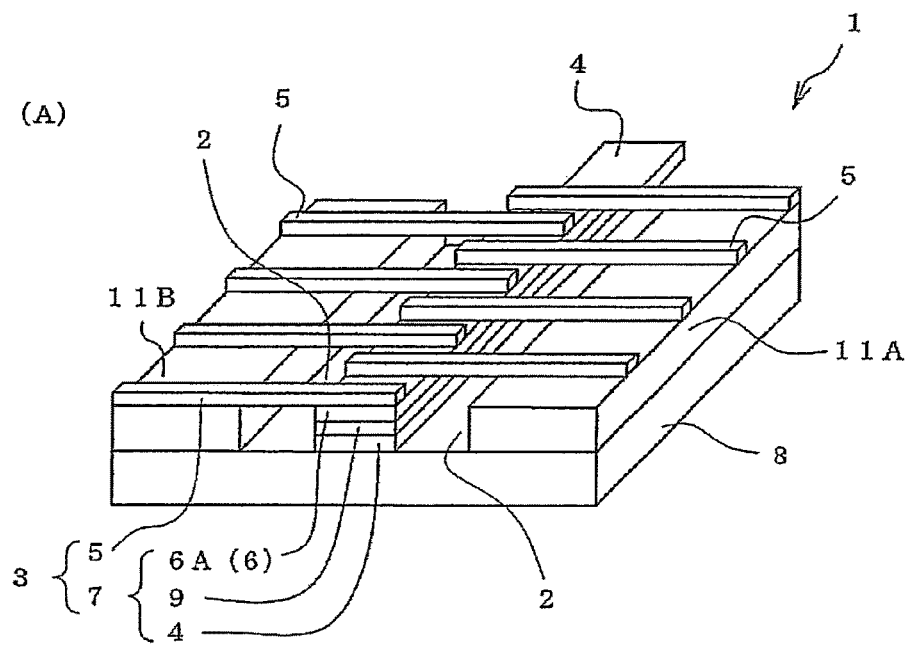
FIG. 1 is a perspective view schematically showing one embodiment of the gas sensor array of the present invention.
Figure 1:
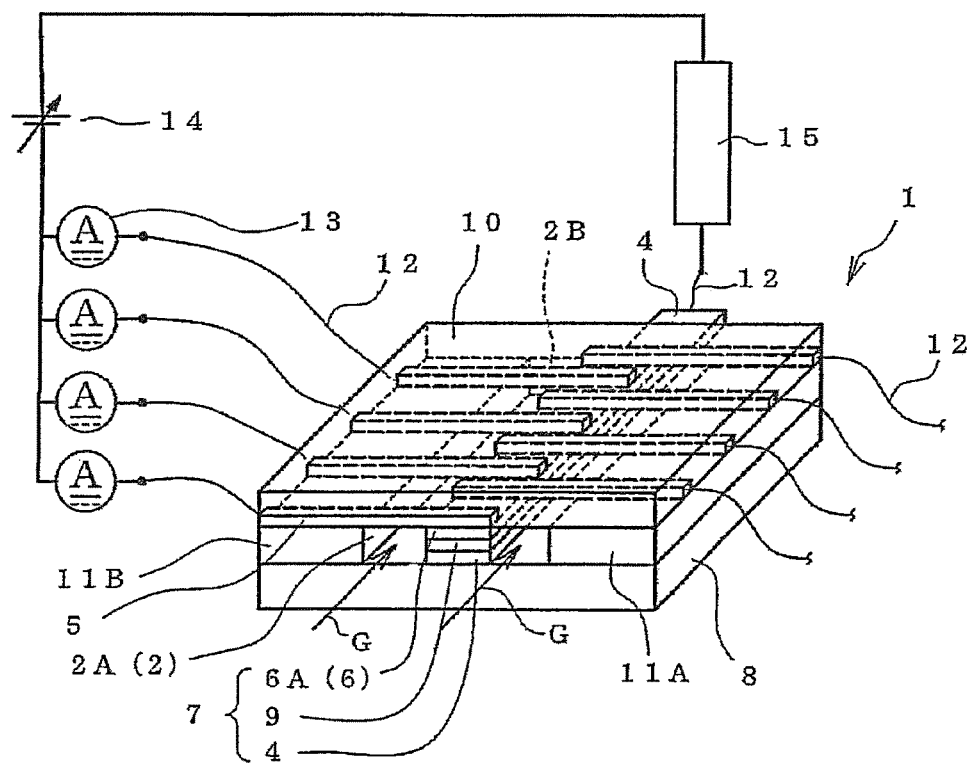

FIG. 1 is a perspective view schematically showing one embodiment of the gas sensor array of the present invention. FIG. 1(A) is a perspective view without a cover, and FIG. 1(B) is a perspective view with a cover.

The gas sensor array of the present invention has, as shown in the gas sensor array 1 in FIG. 1, a gas flow path 2 in which a gas to be analyzed G is flown, and plural gas sensors 3 provided side by side along the gas flowing direction of a gas flow path 2. Here, plural gas sensors 3 each has a constitution wherein semiconductor microcrystals 6 that come into contact with a gas to be analyzed that flows in the gas flow path 2 are provided between two electrodes (first electrode 4 and second electrode 5).

Figure 2:
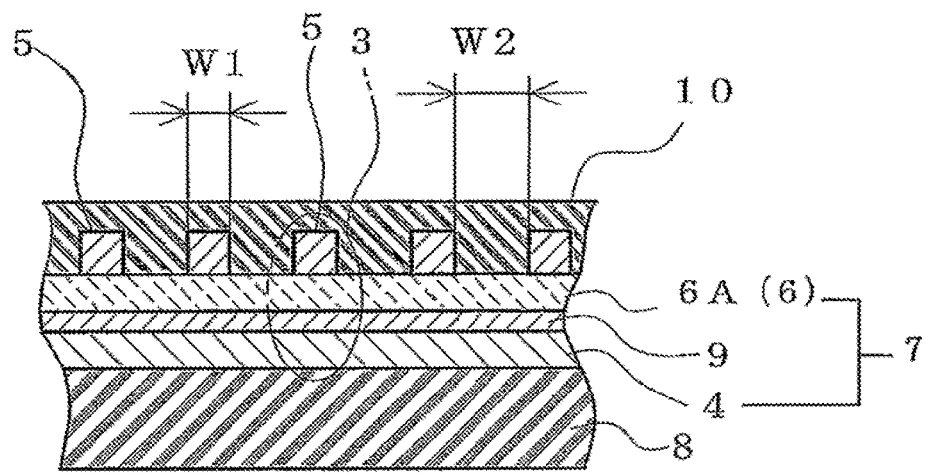
FIG. 2.
Figure 2:
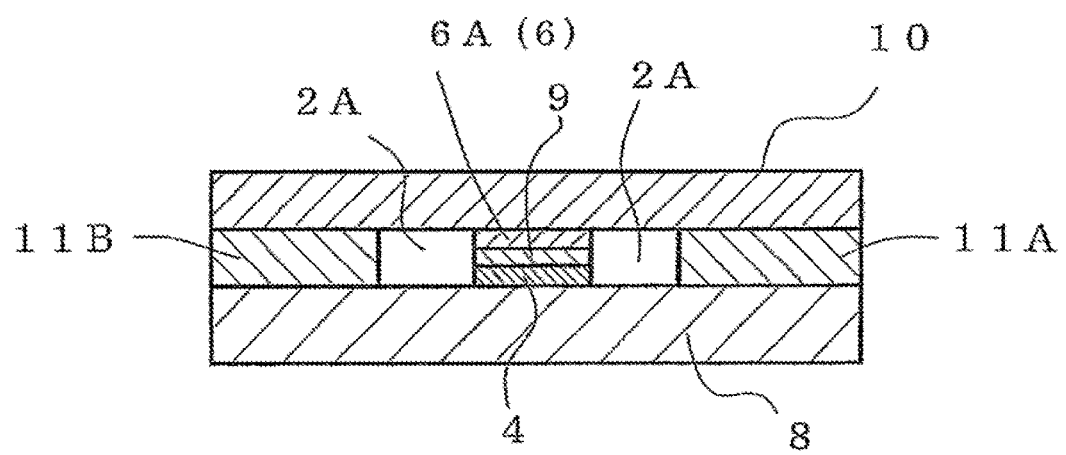

In a preferable embodiment of the gas sensor array of the present invention, as gas sensor array 1 in FIG. 1, plural gas sensors 3 provided side by side along the gas flowing direction of a gas flow path 2 are composed of a laminate 7 wherein an accumulation layer 6A of semiconductor crystals is formed on a first single-electrode 4, a gas flow path 2 configured on the side of the laminate 7 to be in contact with the accumulation layer 6A of semiconductor crystals, and a plurality of second electrodes 5 provided side by side along the gas flowing direction of the gas flow path 2 on the accumulation layer 6A of semiconductor crystals. That is, FIG. 2(A) is a sectional view of the principal part of sensor array 1 wherein a flat plane containing the long axis (gas flowing direction) of laminate 7 shown in FIG. 1 is the section. Beneath each second electrode 5 is formed a gas sensor 3 having a second electrode 5 as one electrode and a first electrode 4 as the other electrode. In FIG. 1, while 8 second electrodes (i.e., 8 gas sensors) are shown, the number is under limitation of space and, in the gas sensor array of the present invention, the number of the second electrodes (i.e., number of gas sensors) is freely set according to the gas measurement environment.

In the embodiment of FIG. 1, plural gas sensors 3 are formed relative to a single laminate 7 wherein an accumulation layer 6A of semiconductor crystals is formed on a single electrode 4. Therefore, a gas sensor array can be produced more easily and one layer of the gas sensor array can be down-sized. In each gas sensor 3, since the electrode on one side sandwiching the semiconductor microcrystal 6 is a single electrode (first electrode 4) common to plural gas sensors, the electric field can be concentrated. In addition, since the side of the accumulation layer 6A of semiconductor crystals is provided in parallel to the gas flowing direction of the gas flow path 2, the accumulation layer 6A of semiconductor crystals has an action like that of an adsorbent in a column of gas chromatography.

While a flat plane shape of the laminate 7 wherein accumulation layer 6A of semiconductor crystals is formed on the first electrode 4 is not particularly limited, in the gas sensor array 1 of FIG. 1, the flat plane shape of the first electrode 4 is band-like, the laminate 7 wherein accumulation layer 6A of semiconductor crystals is formed on the first electrode 4 is band-like, the gas flow path 2 is provided on the side in the short direction of the band-like laminate 7 and along the longitudinal (long axis) direction of the band-like laminate 7, and the axis of a plurality of second electrodes 5 is arranged to be approximately orthogonal to the longitudinal (long axis) direction of the laminate 7. Consequently, the distance between adjacent gas sensors (clearance) can be minimized within the range the independence of the sensor property of individual gas sensor (behavior of electric current change caused by contact of semiconductor microcrystals and gas) can be maintained. Therefore, still more down-sizing of the gas sensor array can be conducted. The axis of a plurality of second electrodes 5 being approximately orthogonal to the longitudinal (long axis) direction of laminate 7 means that an intersection angle formed by the axis of the second electrode 5 and the long axis of laminate 7 is preferably 70 degrees-90 degrees (more preferably 80 degrees-90 degrees, particularly preferably 85 degrees-90 degrees, most preferably 90 degrees).

The gas sensor array of the present invention may consist of individually independent plural gas sensors 3. For example, individually prepared plural gas sensors 3 may be provided on a substrate together with a gas flow path.

Figure 26:
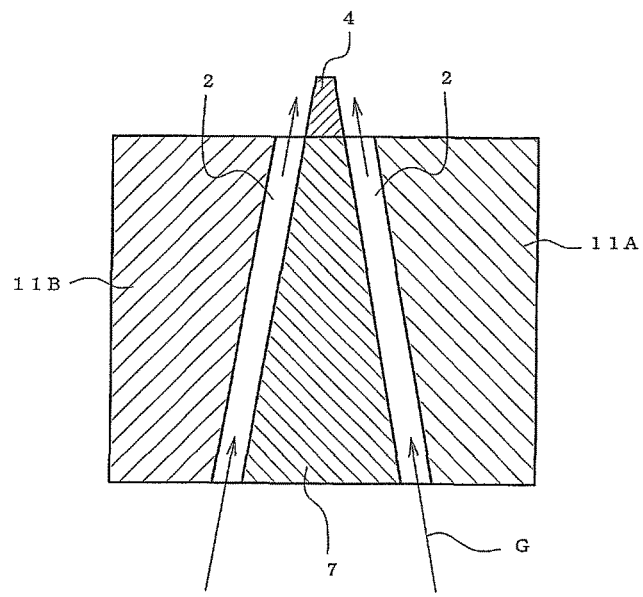
FIG. 26 is a plane view schematically showing another embodiment (modified gas sensor array having two gas flow paths) of the gas sensor array of the present invention.
Figure 27:
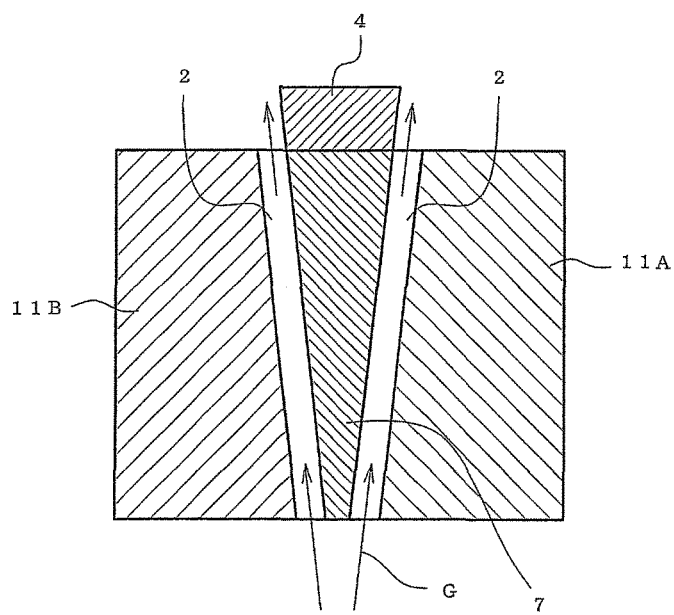
FIG. 27 is a plane view schematically showing another embodiment (modified gas sensor array having two gas flow paths) of the gas sensor array of the present invention.

In the gas sensor array of the present invention, the flat plane shape of the laminate 7 wherein accumulation layer 6A of semiconductor crystals is formed on the first electrode 4 may be square, rhombus, circular, ellipse and the like besides band-like shown in FIG. 1. Since the gas flow path 2 is formed on the side of the laminate 7, flat plane shape of the gas flow path 2 is generally band-like, and may be bending band-like, curved band-like, circular arc-forming band-like and the like besides straight band-like shown in FIG. 1. It may be an embodiment wherein one band-like gas flow path is divided into two band-like gas flow paths, or two band-like gas flow paths are bonded at each one end to form a single thick band-like gas flow path (gas flow path forming a V-shaped or Y-shaped flat plane pattern). The gas flow path 2 may form a ring surrounding the whole circumference of laminate 7. When not less than two band-like gas flow paths 2 are formed, the clearance between adjacent two gas flow paths 2 may gradually become narrower from the downstream side to the upstream side of the flow direction of the gas (FIG. 26), or may gradually become broader from the downstream side to the upstream side of the flow direction of the gas (FIG. 27).

In the gas sensor array 1 of FIG. 1, the accumulation layer 6A of semiconductor microcrystals 6 formed on the first electrode 4 is formed by a method including adhering one surface of a conductive double-sided tape 9 to the first electrode 4, and scattering and pressing semiconductor microcrystals on the other surface of the conductive double-sided tape 9, but the method is not limited thereto. The accumulation layer 6A of semiconductor microcrystals 6 may be directly formed on the first electrode 4 by a method including extending (applying) a dispersion of semiconductor microcrystals in an organic solvent on the first electrode 4 and evaporating the organic solvent and the like. The conductive double-sided tape 9 provided on the first electrode 4 has a function to promote a good ohmic contact of the semiconductor microcrystals to the first electrode 4. It is also possible to form a conductive adhesive layer on the first electrode 4 by using a conductive adhesive instead of the conductive double-sided tape 9, and accumulate and maintain semiconductor microcrystals on the surface of the conductive adhesive layer, whereby the accumulation layer 6A of semiconductor microcrystals 6 is formed. Such constitution also promotes a good ohmic contact of the semiconductor microcrystals to the first electrode 4.

That is, in the present invention, the laminate 7 wherein the accumulation layer 6A of semiconductor crystals is formed on the first electrode 4 preferably has a constitution wherein a conducting layer having adhesiveness or adhesive property is formed on the surface of the first electrode by a conductive double-sided tape or conductive adhesive layer and the like, and the accumulation layer of the semiconductor crystals is formed on the conducting layer. While the thickness of the conducting layer is not particularly limited, it is preferably about 20-100 µm.

Examples of the conductive adhesive constituting the conductive adhesive layer include adhesives containing a conductive powder and an organic binder, and the conductive adhesive is not particularly limited as long as its cured product has conductivity. Examples of the conductive powder include metal simple substance such as copper, gold, silver, nickel, palladium, cobalt and the like, a metal powder of an alloy containing at least one kind selected from the aforementioned metal elements and the like. As the organic binder, one having good adhesive property to a metal is preferable, and examples thereof include epoxy resin, acrylic resin, urethane resin, silicone resin, styrene resin, phenol resin, polyamide resin, polyolefin resin, melamine resin, urea resin and the like. Of these, epoxy resin is preferable in view of connection reliability and the like. As the conductive adhesive, a commercially available product can be used, and a suitable one is selected in consideration of the adhesive property to semiconductor microcrystals and conductivity of cured products. From the aspects of electric and mechanical connection reliability, an epoxy resin conductive adhesive is preferable.

As in the gas sensor array 1 of FIG. 1, plural gas sensors and a gas flow path are generally provided on a substrate in the gas sensor array of the present invention. Substrate 8 is an insulating substrate, and the material constituting same is not particularly limited. For example, curable resins such as epoxy resin, polyimide resin, phenol resin and the like, a composite of curable resin and glass fiber and the like can be mentioned. As the electrode (first electrode 4 and second electrode 5) of a gas sensor, known electrode materials can be applied without particularly limitation and, for example, gold, silver, copper, aluminum, nickel, ITO (indium tin oxide), carbon and the like can be used. The electrode may have a single layer structure or a multi-layer structure. While the thickness of the electrode (total thickness in case of a multi-layer structure) is not particularly limited, it is generally about 20-60 µm. The surface of an electrode is preferably formed from a material having a higher electric conductivity such as gold, silver and the like, more preferably gold. With such an electrode surface, sensing with good Signal-to-Noise Ratio (SN ratio) can be performed. Since the work function of gold (5.2 eV) and the work function of silver (4.73 eV) are comparatively closer to that of selenium (5.9 eV) as compared to the work function of copper (4.65 eV), and particularly, gold is rich in resistance to corrosiveness, an electrode surface more stable and superior in electric contact can be formed.

In the gas sensor array 1 of FIG. 1, two insulating walls 11A, 11B to divide the gas flow path 2 are provided on both sides of the band-like laminate 7 on the substrate 8, and the height of the two walls 11A, 11B is set to be approximately the same as that of the band-like laminate 7. One end of each electrode of the plurality of second electrodes 5 is provided on the band-like laminate 7 and the other end thereof is provided on the wall 11A or wall 11B. That is, the second electrodes 5 are alternately provided by being extended from on top of the band-like laminate 7 to on top of wall 11A, or from on top of the band-like laminate 7 to on top of wall 11B. With such constitution, a lead wire 12 can be easily mounted on each electrode of the plurality of second electrodes 5 and the like. In addition, distribution of the second electrodes 5 to the both sides of the gas flow path 2 facilitates not only identification of even-numbered sensors and odd-numbered sensors from the gas introduction port 2A (see FIG. 2(B)), but also various combinations of sensor distances from the gas introduction port 2A in accordance with the sensor arrival time for each gas type. Furthermore, distribution of the second electrodes 5 to the both sides of the gas flow path enables uniform contact of sensor 3 with the band-like laminate 7 and stable packaging. The insulating wall can be formed by a part of the substrate or independently of the substrate, or may be formed by another body different from the part of the substrate and the substrate. For easiness of production, it is preferably formed by a part of the substrate and an insulator such as an insulating double-sided adhesive sheet and an insulating adhesive.

In the plural gas sensors 3 in the gas sensor array of the present invention, as shown in FIG. 1, a circuit containing an ammeter 13 and a power source 14 is formed for each gas sensor 3, and changes in the electric current produced by the contact of semiconductor microcrystals 6 and a gas is measured (observed) for each gas sensor 3. In FIG. 1(B), symbol 15 is a protective resistance to protect circuits at the time of short circuit. In FIG. 1(B), while only a circuit containing the second electrode 5 on the left side to the paper surface is shown, a circuit containing the second electrode 5 on the right side to the paper surface is in fact formed. However, the circuit is not shown due to the limitation of space.

The gas sensor array of the present invention generally has a cover 10 facing the substrate 8, as shown in FIG. 1(B). The cover 10 prevents leakage of a gas to be analyzed, which flows in the gas flow path 2, from the gas flow path 2, and has a function to fix (maintain) a plurality of second electrodes 5. Cover 10 is specifically composed of a material (curable resin, composite of curable resin and glass fiber etc.) similar to that of the substrate 8, and examples thereof include, but are not limited to, a plate processed or formed to have a concave part receiving the second electrode 5, a laminate wherein an insulation sheet (e.g., epoxy resin adhesive layer, cyanoacrylate adhesion layer etc.) conferred with concave convex followability and a function to adhere and fix an element is laminated on a plate composed of a material (curable resin, composite of curable resin and glass fiber etc.) similar to that of the substrate 8, and the like.

Since the laminate 7 having a laminate constitution of the first electrode 4/conductive double-sided tape 9/accumulation layer 6A of semiconductor crystals has flexibility, a constitution aiming at prevention of a leakage of a gas to be analyzed from the gas flow path 2 can be easily afforded by embedding the second electrode 5 in a concave part of cover 10 (plate having a concave part for receiving second electrode 5) and pressing the substrate 8 and the cover 10 to fix them such that the laminate 7 enters the concave part.

As shown in FIG. 1(A), in the gas sensor array of the present invention 1, the gas flow path 2 has a gas introduction port 2A (see FIG. 2(B)) and a gas discharge port 2B, a gas to be analyzed G flows into the gas flow path 2 from the gas introduction port 2A, and goes outside from the gas discharge port 2B.

In the gas sensor array of the present invention, one or more gas flow paths may be formed. That is, in the gas sensor array 1 of FIG. 1, gas flow path 2 is provided in the transverse direction on both sides of the band-like laminate 7 (i.e., two gas flow paths 2). However, one gas flow path 2 may be provided only on one side of the band-like laminate 7. As in the gas sensor array 1 of FIG. 1, since the constitution wherein a gas flow path is provided in one given direction on both sides of the laminate 7 containing the accumulation layer 6A of semiconductor microcrystals 6 permits exposure of both sides (one side and the other side which is 180 degrees opposite to said side) in one given direction of the accumulation layer 6A of semiconductor crystals to a gas, the gas contact efficiency of the semiconductor microcrystals of each gas sensor 3 can be increased, and each gas sensor 3 has higher sensitivity. Therefore, it is advantageous for affording a gas sensor array with high sensitivity.

Figure 22:
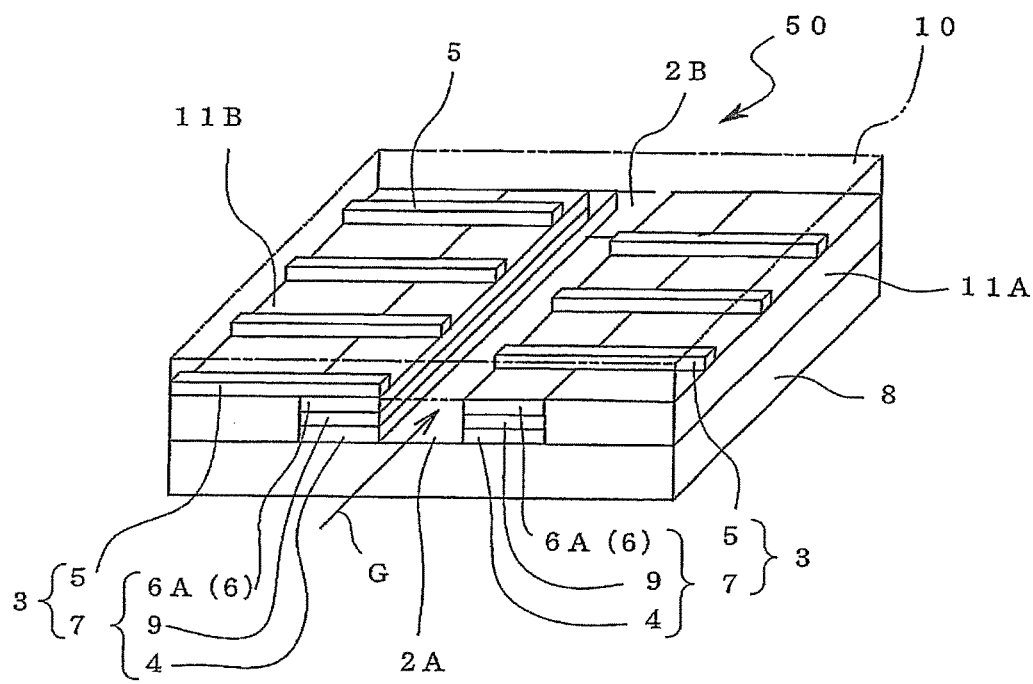
FIG. 22 is a perspective view schematically showing another embodiment (modified gas sensor array having one gas flow path) of the gas sensor array of the present invention.
Figure 23:
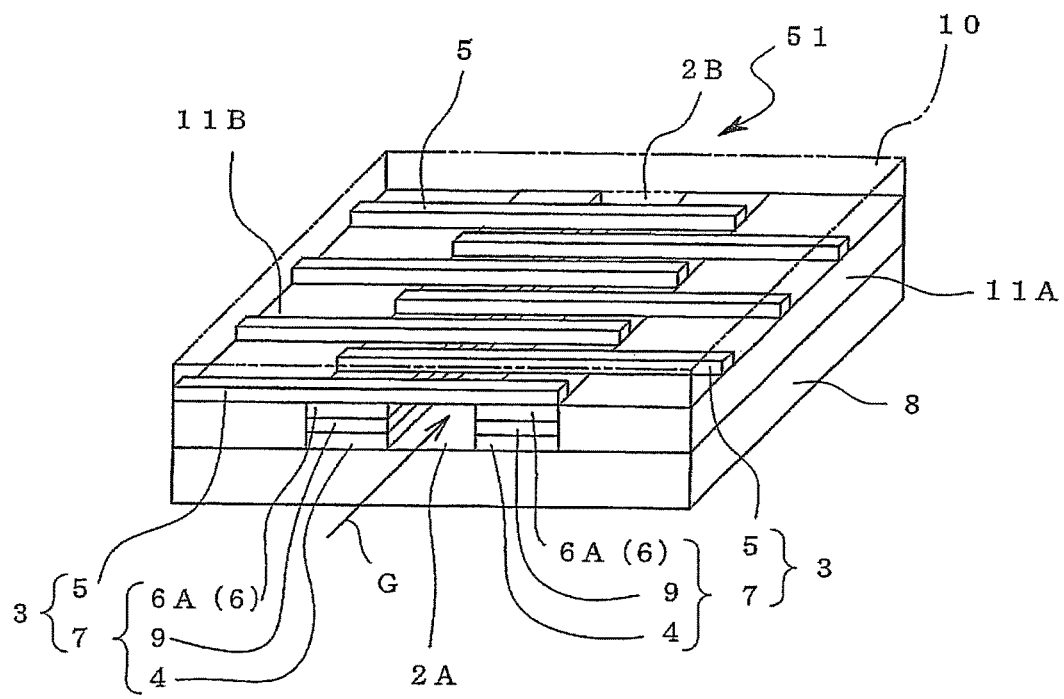
FIG. 23 is a perspective view schematically showing another embodiment (modified gas sensor array having one gas flow path) of the gas sensor array of the present invention.
Figure 24:
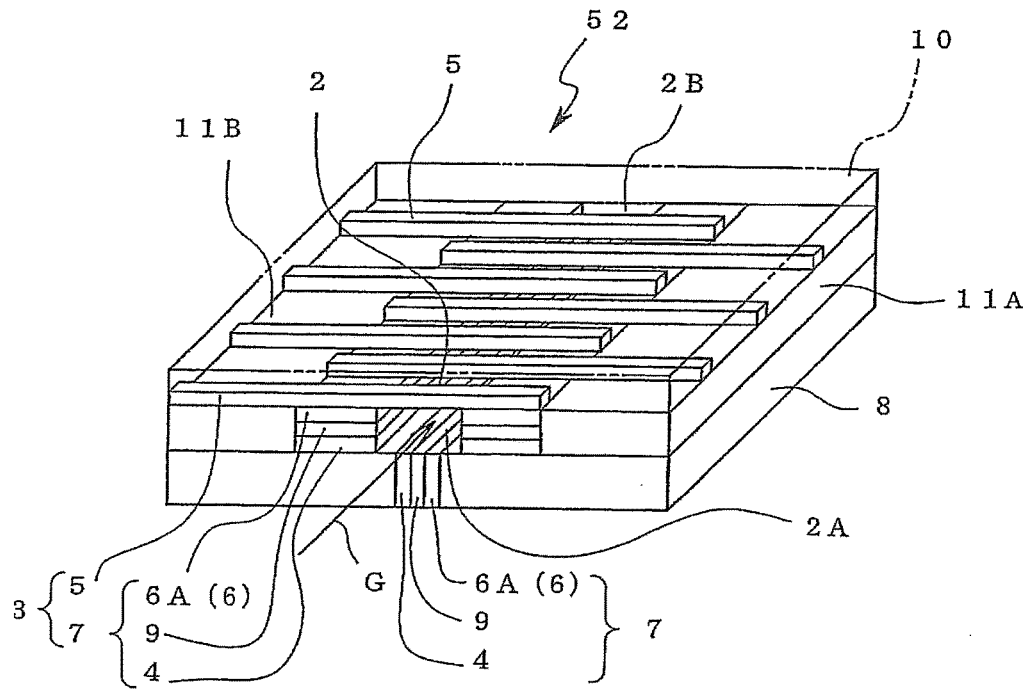
FIG. 24 is a perspective view schematically showing another embodiment (modified gas sensor array having one gas flow path) of the gas sensor array of the present invention.

As a gas sensor array having one gas flow path 2, for example, a constitution in FIG. 1(A) and FIG. 1(B), wherein gas flow path 2 and two insulating walls 11A to divide the gas flow path 2 on one side (side on the right) of laminate 7 are eliminated, and all second electrodes 5 are extended from on top of the laminate 7 to on top of the insulating wall 11B can be mentioned. FIG. 22-FIG. 24 show revised gas sensor arrays having one gas flow path 2. In FIG. 22-FIG. 24, symbols same as those in FIG. 1 (FIG. 1(A) and FIG. 1(B)) mean the same or corresponding parts. In FIG. 22-FIG. 24, for the convenience of explanation, a lead wire, a circuit and the like are not shown, and cover 10 is shown with an imaginary line (two-dot chain line).

In gas sensor array 50 of FIG. 22, a band-like laminate 7 (laminate of first electrode 4/conductive double-sided tape 9/accumulation layer 6A of semiconductor crystals) is formed on both sides of one gas flow path 2 (two band-like laminates 7), insulating walls 11A, 11B are formed outside said laminate, a plurality of second electrodes 5 are alternately provided along the gas flowing direction of the gas flow path 2, on one side and the other side of the gas flow path 2, whereby gas sensor 3 is alternately provided on one side and the other side of the gas flow path 2 along the gas flowing direction of the gas flow path 2. In such gas sensor array 50, the formation pitch (i.e., clearance of adjacent second electrodes 5) of the plural gas sensors 3 formed relative to one band-like laminate 7 can be increased. Therefore, attachment of a lead wire 12 to each electrode of the plurality of second electrodes 5 and the like can be performed with ease. When the formation pitch of the gas sensors 3 is reduced, gas detection at a shorter time interval than the gas sensor array 1 becomes possible. In addition, distribution of the second electrodes 5 to the both sides of the gas flow path 2 facilitates not only identification of even-numbered sensors and odd-numbered sensors from the gas introduction port 2A of the gas flow path 2 (see FIG. 2(B)), but also various configuration forms of the second electrode which variously change the distance from the gas introduction port 2A to each gas sensor 3. Furthermore, distribution of the second electrodes 5 to the both sides of the gas flow path 2 (gas sensors 3 are distributed to both sides of gas flow path 2) enables uniform contact of gas sensor 3 with the band-like laminate 7 and stable packaging.

In the gas sensor array 50 of FIG. 22, second electrodes 5 are arranged such that plural gas sensors 3 are alternately distributed to the both sides of the gas flow path 2 in the order of increasing clearance from the introduction port 2A of the gas flow path 2. Alternatively, second electrodes 5 on the both sides of the gas flow path 2 may be disposed at opposing positions facing the gas flow path 2. In this case, since the gas sensors specified by the clearance from the introduction port 2A of the gas flow path 2 (gas sensors specified by the order from the gas introduction port 2A of the gas flow path 2) is constituted of two opposing gas sensors facing the gas flow path 2, sensing with good Signal-to-Noise Ratio (SN ratio) as compared to one gas sensor provided on one side of the gas flow path 2 can be performed by superposing signals of the two gas sensors. By changing the formation pitch of the plurality of second electrodes 5 provided on one side of a gas flow path and that of the plurality of second electrodes 5 provided on the other side of a gas flow path, the gas sensor group on one side of the gas flow path and the gas sensor group on the other side of the gas flow path can also be used as independent gas sensor array for a particular gas type.

The gas sensor array 51 of FIG. 23 is different from the gas sensor array 50 of FIG. 22 in that each electrode of the plurality of second electrodes 5 is extended to stay on two band-like laminates 7 provided on the both sides of the gas flow path 2. Since such gas sensor array 51 includes individual gas sensors 3 containing two accumulation layers 6A of semiconductor crystals, sensing with good Signal-to-Noise Ratio (SN ratio) as compared to sensor configuration only on one side can be advantageously performed by superposing signals of the right and left sensors (two gas sensors on one side and the other side of gas flow path 2), which are at the same clearance from the introduction port of the gas flow path 2.

The gas sensor array 52 of FIG. 24 is different from the gas sensor array 51 of FIG. 23 in that a band-like laminate 7 (laminate of first electrode 4/conductive double-sided tape 9/accumulation layer 6A of semiconductor microcrystals 6) is embedded in the bottom surface of the gas flow path 2 of the substrate 8 such that the side of the accumulation layer 6A of semiconductor crystals appears within the gas flow path 2. Such gas sensor array 52 is a constitution advantageous for the measurement of a gas type that easily settles to the bottom of the gas flow path such as carbon dioxide, since the side of the accumulation layer 6A of semiconductor crystals appears on the side and bottom of the gas flow path. In addition, by providing a second electrode (not shown) formed relative to the band-like laminate 7 incorporated into the substrate 8 at a formation pitch (arrangement interval) different from that of the plurality of second electrodes 5 provided on the both sides of the gas flow path 2, it can also be used as a sensor array independent of the gas sensor array constituted of plural gas sensors 3 wherein plural gas sensors relative to the band-like laminates 7 incorporated in the substrate 8 are provided on the both sides of the gas flow path 2.

Figure 25:
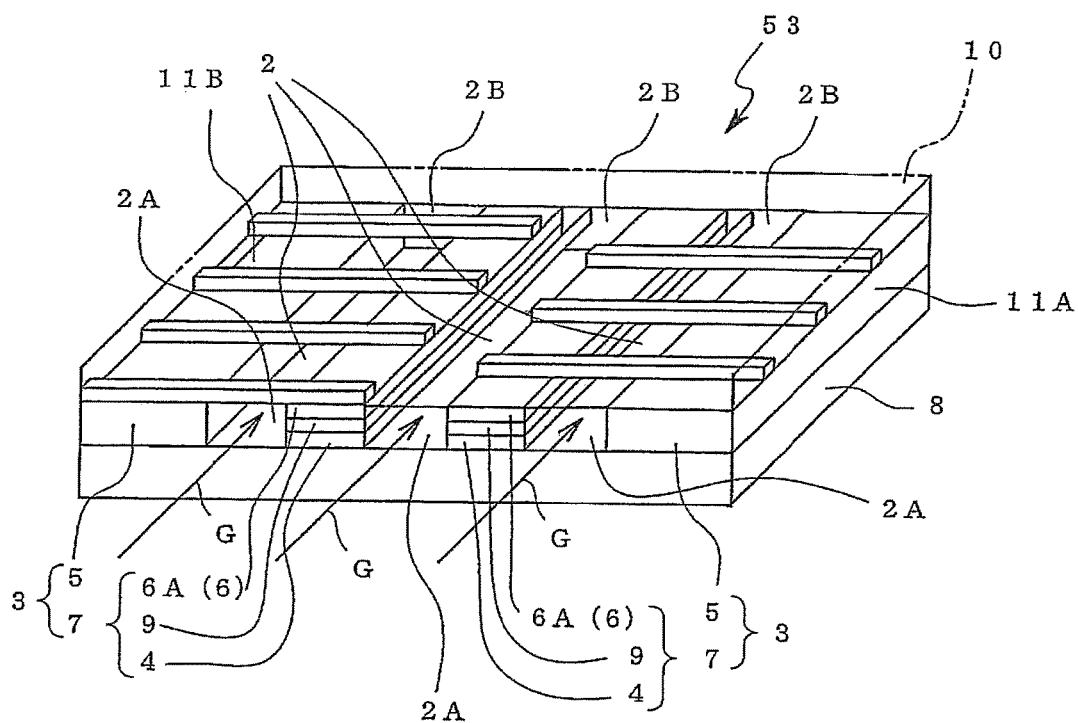
FIG. 25 is a perspective view schematically showing another embodiment (modified gas sensor array having three gas flow paths) of the gas sensor array of the present invention.

FIG. 25 shows a gas sensor array having three gas flow paths. The symbols same as those in FIG. 1 (FIG. 1(A) and FIG. 1(B)) mean the same or corresponding parts. In FIG. 25, for the convenience of explanation, a lead wire, a circuit and the like are not shown, and cover 10 is shown with an imaginary line (two-dot chain line). In the gas sensor array 53 of FIG. 25, one gas flow path 2 is formed between two band-like laminates 7 (laminate of first electrode 4/conductive double-sided tape 9/accumulation layer 6A of semiconductor crystals), one gas flow path 2 is formed between one band-like laminate 7 and insulating wall 11A, and between the other band-like laminate 7 and insulating wall 11B, totaling 3 gas flow paths 2. Then, a plurality of second electrodes 5 are alternately provided relative to two band-like laminates 7 sandwiching the central gas flow path 2, along the gas flowing direction of the gas flow path 2, whereby plural gas sensors 3 are provided along the gas flowing direction of the gas flow path 2.

In such gas sensor array 53, gas flow paths 2 are formed on both sides of two band-like laminates 7 (laminate of first electrode 4/conductive double-sided tape 9/accumulation layer 6A of semiconductor crystals), and the formation pitch (clearance of adjacent second electrodes 5) of the plural gas sensors 3 formed relative to one band-like laminate 7 can be increased. Therefore, attachment of a lead wire 12 to each electrode of the plurality of second electrodes 5 and the like can be advantageously performed with ease. As compared to the gas sensor array 50 of FIG. 22, since gas flow paths are formed on both sides of one band-like laminate 7, sensing with good Signal-to-Noise Ratio (SN ratio) can be performed. When the formation pitch (i.e., clearance between adjacent second electrodes 5) of the gas sensors 3 is reduced, gas detection at a shorter time interval than the gas sensor array 1 of FIG. 1 advantageously becomes possible. In addition, distribution of the second electrodes 5 to the both sides of the gas flow path 2 facilitates not only identification of even-numbered sensors and odd-numbered sensors from the gas introduction port 2A of the gas flow path 2 (see FIG. 2(B)), but also various configuration forms of the second electrode which variously change the distance from the gas introduction port 2A to each gas sensor 3. Furthermore, distribution of the second electrodes 5 to the both sides of the gas flow path 2 (gas sensors 3 are distributed to both sides of gas flow path 2) enables uniform contact of gas sensor 3 with the band-like laminate 7 and stable packaging.

In the gas sensor array 53 of FIG. 25, plural second electrodes 5 are arranged such that plural gas sensors 3 are alternately distributed to the both sides of the central gas flow path 2 in the order of increasing clearance from the introduction port 2A of the gas flow path 2. Alternatively, second electrodes 5 on the both sides of the central gas flow path 2 may be disposed at opposing positions facing the central gas flow path 2. In this case, since the gas sensors specified by the clearance from the introduction port 2A of the central gas flow path 2 (gas sensors specified by the order from the gas introduction port 2A of the gas flow path 2) is constituted of two opposing gas sensors facing the central gas flow path 2, sensing with good Signal-to-Noise Ratio (SN ratio) as compared to one gas sensor provided on one side of the gas flow path 2 can be performed by superposing signals of the two gas sensors. By changing the formation pitch of the plurality of second electrodes 5 provided on one side of the central gas flow path 2 and that of the plurality of second electrodes 5 provided on the other side of a gas flow path, the gas sensor group on one side of the central gas flow path and the gas sensor group on the other side can also be used as independent gas sensor array for a particular gas type.

As in the gas sensor array 51 of FIG. 23, each electrode of the plurality of second electrodes 5 may be extended to stay on two band-like laminates 7. In this case, sensing with good Signal-to-Noise Ratio (SN ratio) as compared to sensor configuration only on one side can be advantageously performed by superposing signals of the right and left sensors (two gas sensors on one side and the other side of the central gas flow path 2.

While FIG. 1 and FIG. 22-FIG. 25, gas sensor arrays with 1 to 3 gas flow paths (gas flow path parallel to each other in the case of 2-3 paths) are shown, for example, when a gas sensor array has a gas flow path having a V-shaped or Y-shaped flat pattern, since the gas flow increases from near the terminal part (near meeting part of two gas flow paths) on the opposite side from the gas introduction port of the two gas flow paths and a single gas flow path after merging thereof, low sensitivity of a gas sensor at the downstream of the gas flowing direction of the gas flow path can be advantageously compensated for.

In the gas sensor array of the present invention, the semiconductor microcrystal 6 to be used for the gas sensor 3 is not particularly limited and any can be used as long as it has property that an electric current flows when placed under a constant voltage and impedance increases and an electric current value decreases by making contact with a gas molecule at room temperature. In view of high sensitivity to gas molecule, particularly organic gas molecule, microcrystalline selenium is preferable. The "microcrystal" in the present invention means a crystal having a long axis length (long diameter) of several dozen µm or below.

The microcrystalline selenium is obtained by contacting amorphous selenium with an organic solvent at room temperature at least for several minutes to allow crystal growth (self-growth) from amorphous selenium. Amorphous selenium is generally used by grinding to a fine powder having a particle size of about 20-30 µm. As an organic solvent to be contacted with amorphous selenium, a solvent having a relative permittivity (room temperature) of higher than 4.0, for example, acetone, pyridine, ethanol, methanol, 2-propanol, acetonitrile, diethyl ether, benzylamine, piperidine, aniline, quinoline, acetophenone, benzonitrile and the like, and a solvent having a relative permittivity (room temperature) of lower than 4.0, for example, benzene, toluene, cyclohexane, hexane and the like are used.

When an organic solvent having a relative permittivity (room temperature) of higher than 4.0 is used as an organic solvent, a selenium nanowire having a nano size (generally several nm-800 nm), which is fibrous or needle-shaped hexagonal microcrystalline selenium having a length of about 1-10 µm, is produced. When an organic solvent having a relative permittivity (room temperature) of lower than 4.0 is used, microcrystalline selenium comprised of granular monoclinic polyhedron having a particle size of about 1-10 µm is produced. Microcrystalline (hexagonal system) selenium grown in a moderate curve is called "fibrous", microcrystalline (hexagonal system) selenium grown linear and rather short is called "needle-shaped", and the "selenium nanowire" is a concept including either of both of these. The "room temperature" in the present specification generally means the range of 20-25° C. Even when monoclinic selenium is used instead of amorphous selenium, microcrystalline selenium can be produced in a similar manner.

The fibrous or needle-shaped hexagonal microcrystalline selenium (hereinafter to be also simply referred to as "selenium nanowire") has the intrinsic properties of a P-type semiconductor, is extremely stable (that is, a stable crystal form), and maintains the nano-sized fibrous or needle-shaped form even at high temperatures and low temperatures. The shape and size of a selenium nanowire (thickness, length), and particle size and the like of microcrystalline selenium consisting of granular monoclinic polyhedron can be controlled by the kind of an organic solvent to be contacted with amorphous selenium, a method of contacting with an organic solvent, work environments (temperature, pressure) and the like. As for the adjustment of the shape and size of microcrystalline selenium, WO 2011/055751 (patent document 1) by the present applicant can be referred to.

When microcrystalline selenium is placed at a fixed voltage at room temperature, a certain amount of electric current flows through a selenium nanowire due to the electric conductivity mechanism based on the intrinsic properties of selenium as a P-type semiconductor. In addition, monoclinic microcrystalline selenium itself is an insulator, but a certain amount of electric current flows, though the current value is smaller than that of a selenium nanowire, presumably because of smaller grain diameter and surface conductivity due to a dirty surface. When an organic gas molecule contacts microcrystalline selenium at room temperature, the organic gas molecule adsorbs to microcrystalline selenium to increase impedance of microcrystalline selenium, which in turn decreases the electric current value. When the organic gas is removed, the current value increases and microcrystalline selenium is restored to the state before contact with the organic gas. Therefore, by providing microcrystalline selenium between two electrodes, a gas sensor capable of sensing (detecting) an organic gas can be produced. Of microcrystalline selenium, selenium nanowire shows extremely high reaction sensitivity with an organic gas molecule, and fast response rates of decrease and increase (restoration) of the electric current value. Therefore, by applying selenium nanowire as the semiconductor microcrystal of the gas sensor 3, a gas sensor with high sensitivity can be obtained.

In the gas sensor array of the present invention, the area of the part that senses a gas in each gas sensor 3, i.e., the part where two electrodes (first electrode 4 and second electrode 5) sandwiching the semiconductor microcrystal overlap via the semiconductor microcrystal, is about 0.1-1.5 mm$^2$, preferably about 0.2-0.5 mm$^2$. The amount of semiconductor microcrystal interlaid between two electrodes (first electrode 4 and second electrode 5) is preferably about 20-100 μg/mm$^2$.

While the shape and size of the gas flow path 2 is not particularly limited, the cross section of the gas flow path 2 (section perpendicular to the axis of gas flow path 2) is generally a square or rectangle having an area of about 0.05-0.8 mm$^2$, and the length of the gas flow path is generally about 5.0-10.0 mm (preferably about 5.0-8.9 mm). While the gas flow path 2 is generally a linear path divided by a wall, it may be a simple space difficult to define as a linear path since a gas flow only needs to be formed.

The sensor operation of individual gas sensor 3 in the gas sensor array of the present invention is generally performed by setting clearance between two electrodes (first electrode 4 and second electrode 5) to about 0.10-0.30 mm, and applying a voltage of about 1-15V between two electrodes. The voltage is about 1-15V, preferably about 3-7V. For example, when 5V is applied, the gas comes into contact with semiconductor microcrystals and a constant current of about 40-120 μA flows through individual gas sensors. When the gas comes into contact with semiconductor microcrystals sandwiched by two electrodes, the electric current value decreases, and when the contact of the organic gas with the semiconductor microcrystal disappears, the current value restores to the original state.

Figure 3:
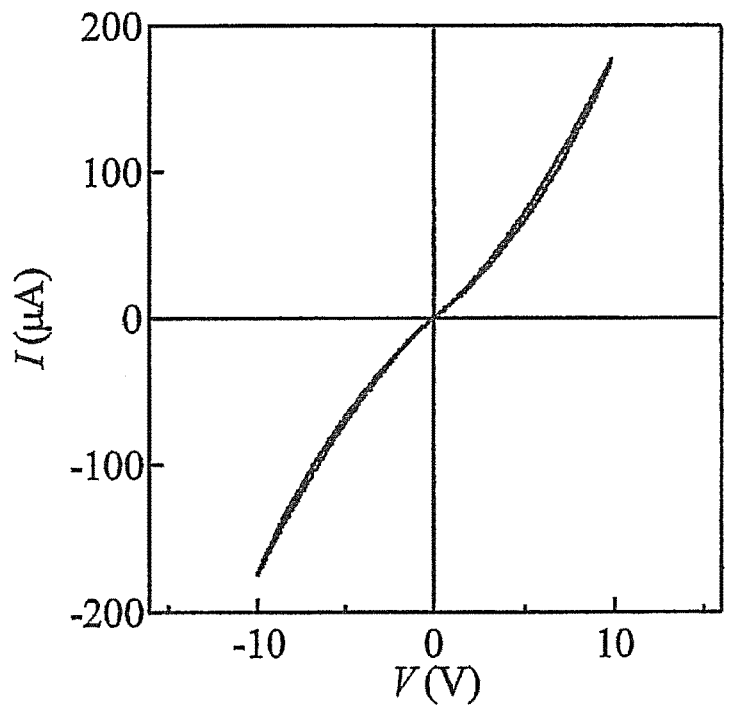
FIG. 3 shows electric current-voltage property of a gas sensor (simple substance) constituting the gas sensor array of the present invention.
Figure 4:
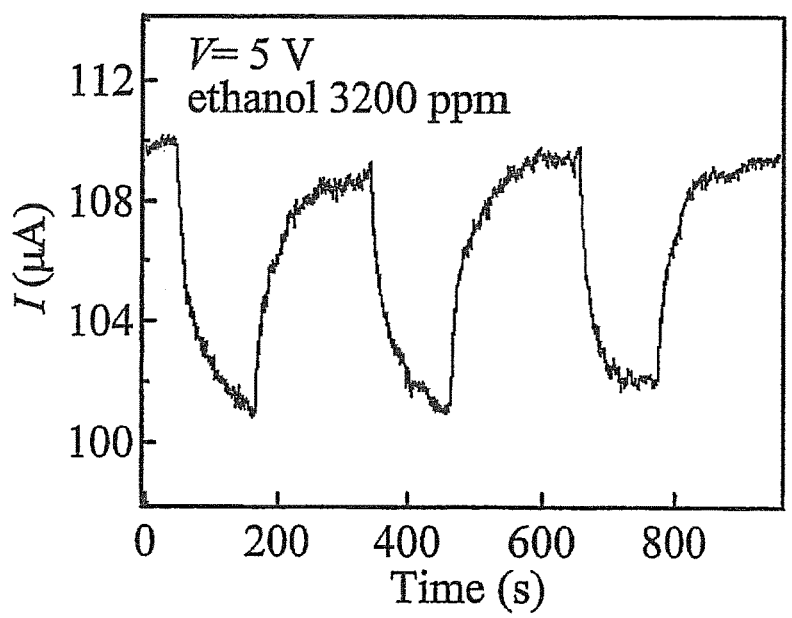
FIG. 4 shows ethanol gas sensitivity of a gas sensor (simple substance) constituting the gas sensor array of the present invention.
Figure 5:
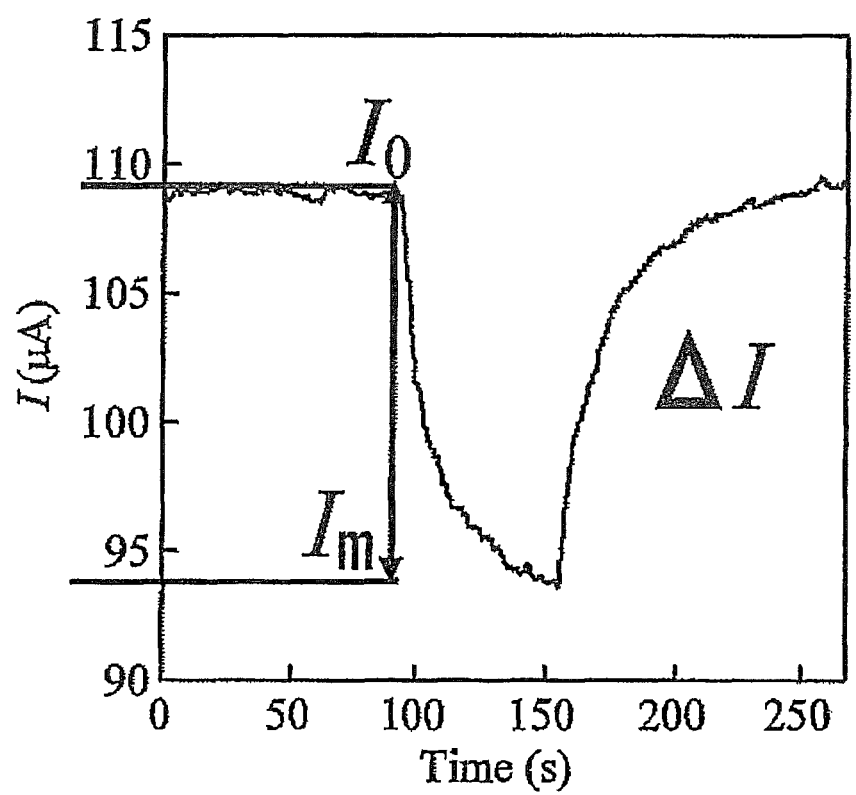
FIG. 5 is a partially enlarged view of FIG. 4.

For example, FIG. 3 shows voltage-current characteristics of a gas sensor 3 using selenium nanowires (thickness: 23.3 nm, length: 4 μm) as semiconductor microcrystal to be provided between two electrodes (first electrode 4 and second electrode 5) at room temperature (atmosphere), and FIG. 4 shows changes in the electric current value I when 5V fixed voltage is applied between two electrodes (first electrode 4 and second electrode 5) of gas sensor 3 and 5 L of air containing 100 μL of ethanol gas is intermittently contacted with the semiconductor microcrystal (selenium nanowire) sandwiched between the two electrodes. FIG. 5 is a partially enlarged view of FIG. 4. In FIG. 5, $I_0$ is an initial electric current value flowing in the gas sensor before contact of semiconductor microcrystal (selenium nanowire) with an organic gas (ethanol gas), $I_m$ is a minimum electric current value, and ΔI is an amount of decrease in the electric current value.

Sensor response (S) of one gas sensor 3 is shown by the following formula.

$$S=(I_0-I_m)/I_0=\Delta I/I_0 \qquad [\text{number 1}]$$

Sensor response (S) is obtained by normalizing an amount of current value decrease $\Delta I=(I_0-I_m)$ due to organic gas to the initial current value $I_0$.

The change behavior of the electric current due to the contact of semiconductor microcrystal and a gas under a constant voltage in one gas sensor 3 varies depending on the kind of the organic gas to be contacted with the semiconductor microcrystal. Therefore, the kind of gas can be distinguished from the difference in the size of change of the electric current under a constant voltage in gas sensor 3.

Figure 6:
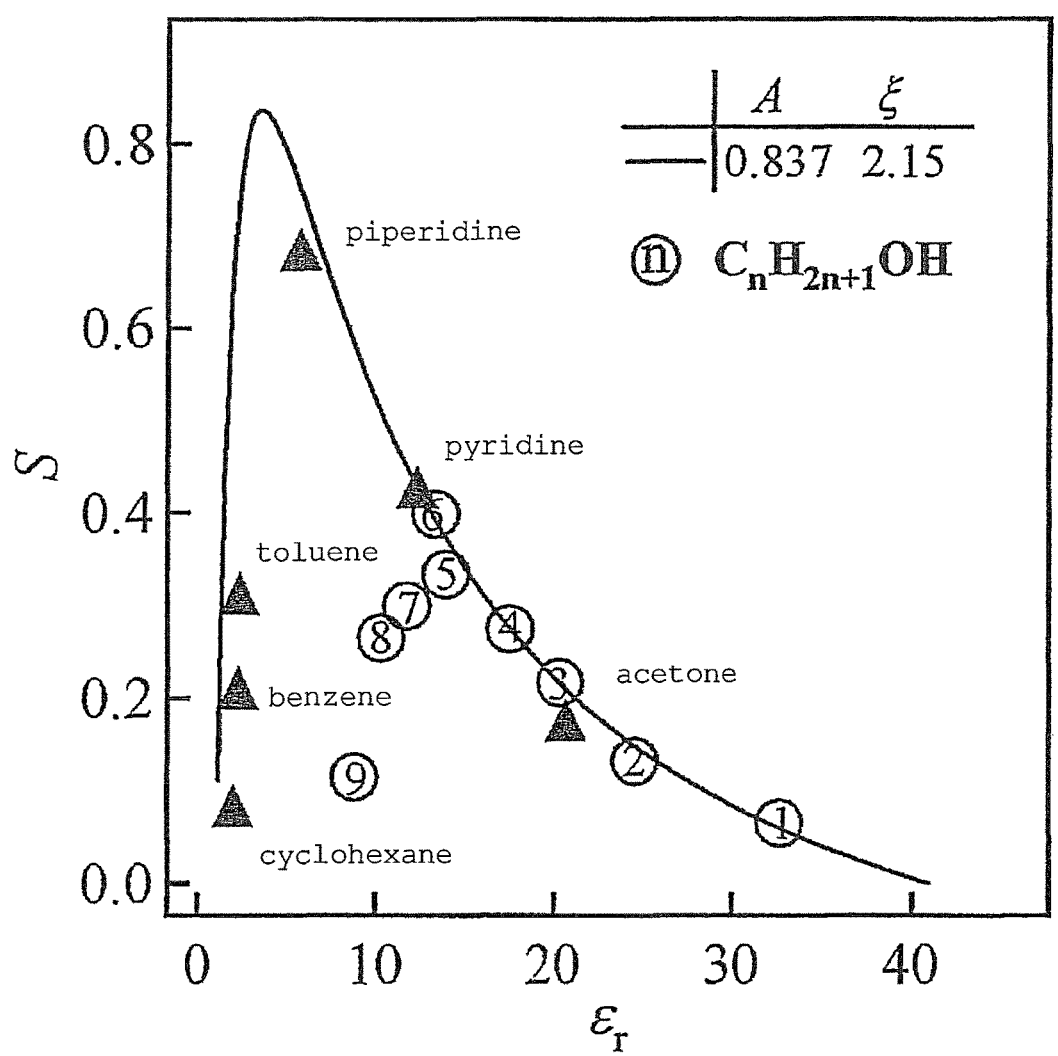
FIG. 6 shows the detection sensitivity (sensor response S) of a gas sensor constituting the gas sensor array of the present invention to various organic gases, in relation to the dielectric constant $\in_r$ of the solvent of the organic gas.

FIG. 6 shows detection sensitivity of gas sensor 3 to various organic gases. The sensor response (S(N)) of gas sensor 3 to a concentration (N) of a gas to be analyzed can be shown by the following formula.

$$S(N) = A\xi\left(\frac{\epsilon_r-1}{\epsilon_r+2}\right)\left[2-\xi\left(\frac{\epsilon_r-1}{\epsilon_r+2}\right)\right] \qquad [\text{number 2}]$$

$$\xi = (3V/d)N^n/N_m$$

wherein, $\epsilon_r$ is a dielectric constant of an organic gas (dielectric constant of stock solution of commercially available organic solvent), A is a contact efficiency of selenium nanowire and gas, V is voltage, d is distance between electrodes, N is concentration, n is an exponent, and $N_m$ is a concentration of a stock solution of a commercially available organic solvent.

When $2 \gg \xi(\epsilon_r-1)/(\epsilon_r+2)$ stands, the sensor response can be shown by the following formula.

$$S(N)=S(N_m)N_x^n \qquad [\text{number 3}]$$

wherein $N_X$ is a concentration $N/N_m$ standardized to $N_m$ of organic gas.

The curve in FIG. 6 is fitting by the above-mentioned formula [number 2] wherein A=0.837, ξ=2.15, the vertical axis is sensor response (S=ΔI/I$_0$) and the horizontal axis is dielectric constant ($\epsilon_r$) of organic gas.

As is clear from FIG. 6, organic gases (e.g., benzene and acetone) showing similar detection sensitivity (sensor response S) values are not easy to distinguish. The circled numbers in FIG. 6 are plotted to show detection sensitivity of straight chain aliphatic primary alcohol having a carbon number corresponding to said number, from which it is clear that 1-octanol and 1-butanol have similar detection sensitivity S and cannot be distinguished with ease. However, the gas sensor array of the present invention can distinguish them, as mentioned below.

The gas sensor array of the present invention is, as described above, characterized by a gas flow path 2 in which a gas to be analyzed G is flown, and plural gas sensors 3 provided side by side along the gas flowing direction of a gas flow path 2. With such constitution, since plural gas sensors 3 have a different distance from the gas introduction port 2A of the gas flow path 2, when a gas is introduced into the gas flow path 2 from the gas introduction port 2A, a time shift occurs in the time-change spectrum of electric current change ($I/I_0$) of each gas sensor.

Figure 7:
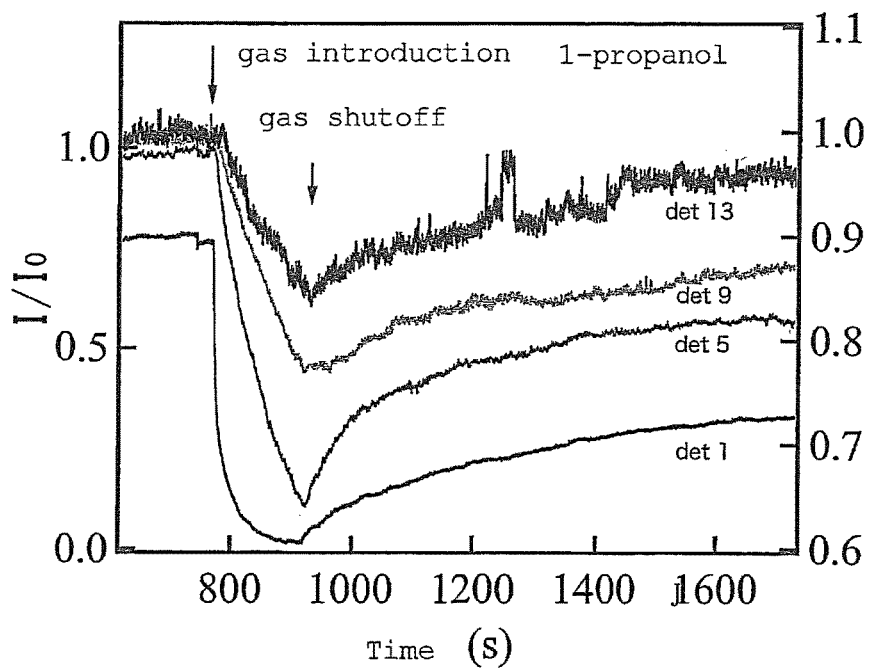
FIG. 7.
Figure 7:
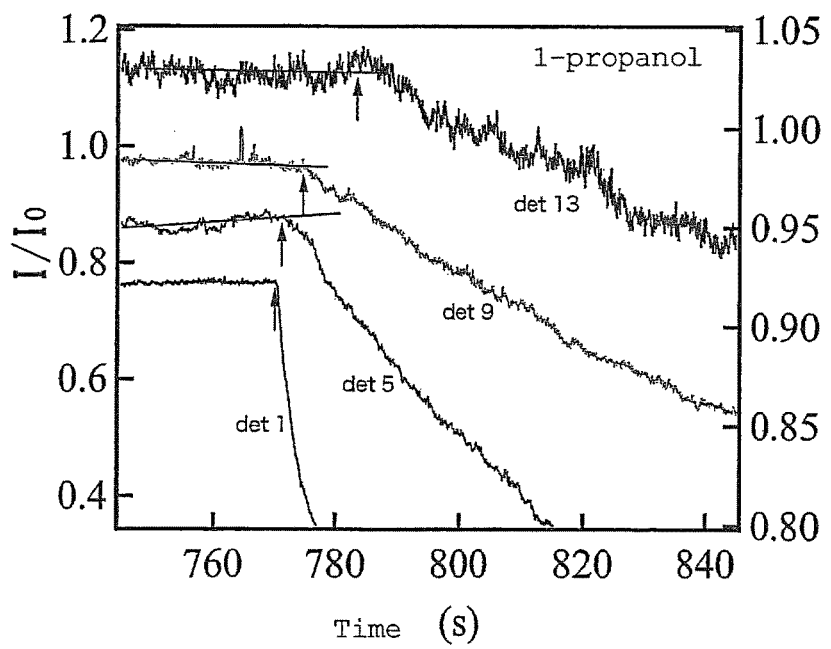

FIG. 7(A) and FIG. 7(B) show time-change spectra of electric current change ($I/I_0$) in the first gas sensor (det 1), the fifth gas sensor (det 5), the ninth gas sensor (det 9) and the thirteenth gas sensor (det 13), counting from the gas introduction port 2A of the gas flow path 2, when the gas sensor array 1 having the constitution shown in FIG. 1, wherein 15 gas sensors were provided side by side, which was obtained in the below-mentioned Experimental Example, was used and 1-propanol was flown in the gas flow path 2 as an organic gas. FIG. 7(A) is a figure on the scale showing the elapsed time of test including the time from the start of introduction of a gas into the gas flow path to the completion of the gas introduction on the horizontal axis, and FIG. 7(B) is a figure on the scale showing the start of introduction of a gas into the gas flow path (760 sec-840 sec from the start of test) on the horizontal axis. The vertical axis on the left of FIG. 7(A) and FIG. 7(B) is the scale for the first gas sensor (det 1), and the axes on the right is the scale for the fifth gas sensor (det 5), the ninth gas sensor (det 9) and the thirteenth gas sensor (det 13). Each spectrum is shown by sliding in the vertical axis direction to avoid superposition.

From FIG. 7(B), it is clear that the time when a decrease in the electric current starts on contact of semiconductor microcrystal with a gas (that is, reaction start time), specified with arrows therein, is delayed in the order of the first gas sensor (det 1), the fifth gas sensor (det 5), the ninth gas sensor (det 9), and the thirteenth gas sensor (det 13), in the time-change spectra of electric current change ($I/I_0$) of individual gas sensors.

Figure 8:
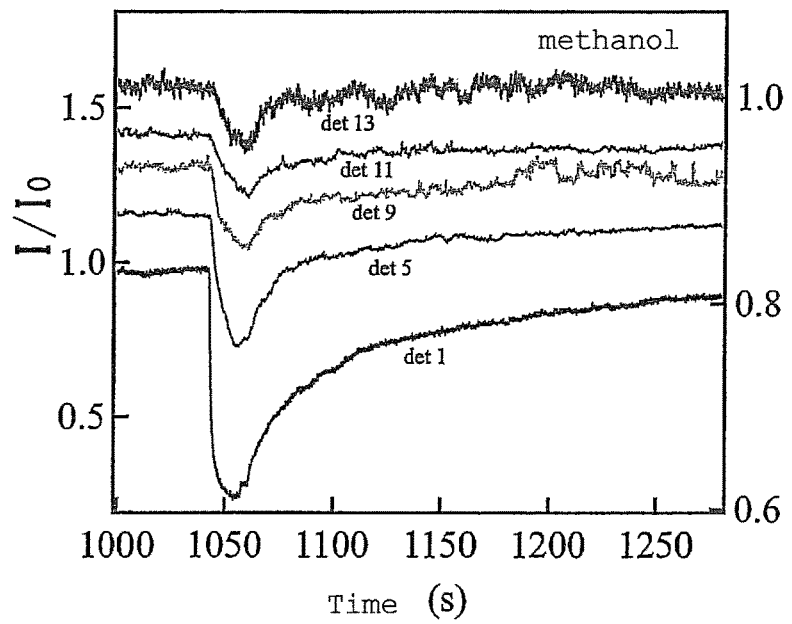
FIG. 8.
Figure 8:
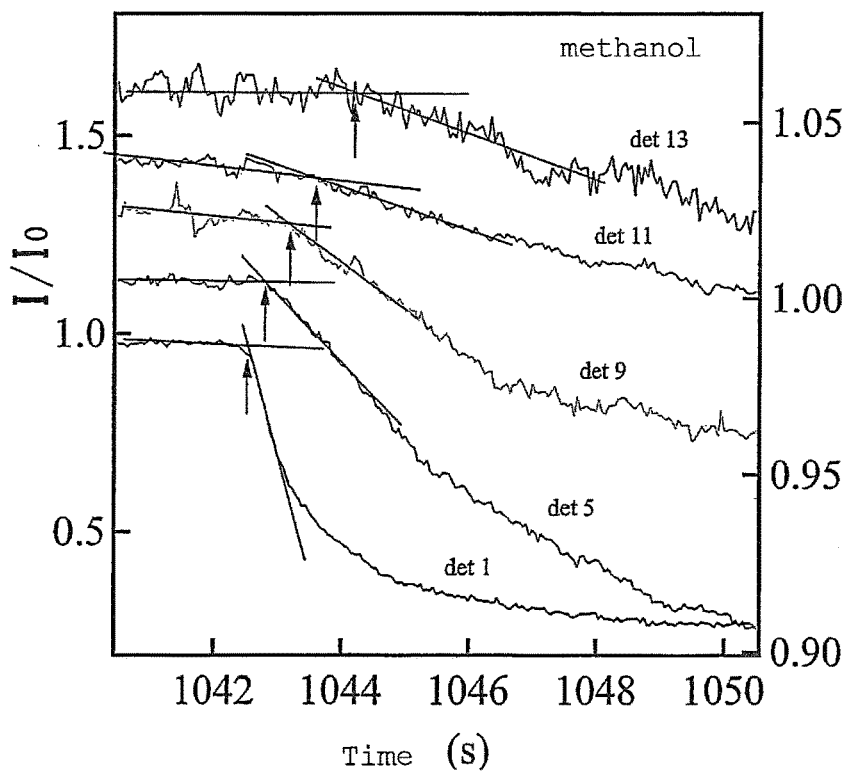

Similarly, FIG. 8(A) and FIG. 8(B) show time-change spectra of electric current change ($I/I_0$) in the first gas sensor (det 1), the fifth gas sensor (det 5), the ninth gas sensor (det 9), the eleventh gas sensor (det 11) and the thirteenth gas sensor (det 13), counting from the gas introduction port 2A of the gas flow path 2, when the gas sensor array 1 having the constitution shown in FIG. 1, wherein 15 gas sensors 3 were provided side by side was used and methanol was flown in the gas flow path 2 as an organic gas. FIG. 8(A) is a figure on the scale showing the elapsed time of test including the time from the start of introduction of a gas into the gas flow path to the completion of the gas introduction on the horizontal axis, and FIG. 8(B) is a figure on the scale showing the start of introduction of a gas into the gas flow path (1042 sec-1050 sec from the start of test) on the horizontal axis. The vertical axis on the left of FIG. 8(A) and FIG. 8(B) is the scale for the first gas sensor (det 1), and the axes on the right is the scale for the fifth gas sensor (det 5), the ninth gas sensor (det 9) and the thirteenth gas sensor (det 13). Each spectrum is shown by sliding in the vertical axis direction to avoid superposition.

Figure 9:
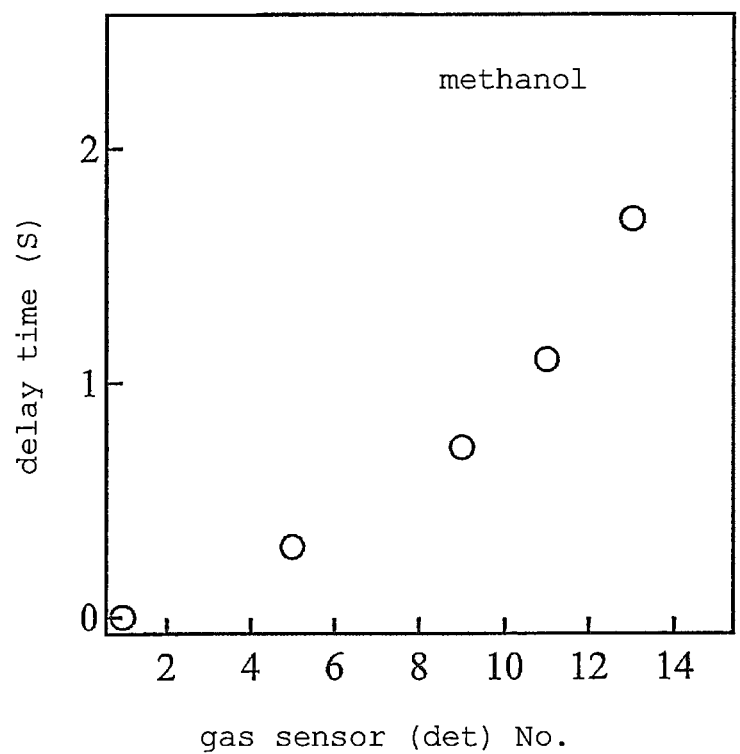
FIG. 9 shows the relationship between a delay time in the start of a reaction of time-change spectrum of electric current change ($I/I_0$) in plural gas sensors in the gas sensor array of the present invention relative to methanol gas, and the position of gas sensors (position of gas flowing direction of gas flow path, gas sensor (det) No.).

From FIG. 8(B), it is clear that the time when a decrease in the electric current starts on contact of semiconductor microcrystal with a gas (that is, reaction start time), specified with arrows therein, is delayed in the order of the first gas sensor (det 1), the fifth gas sensor (det 5), the ninth gas sensor (det 9), the eleventh gas sensor (det 11), and the thirteenth gas sensor (det 13), in the time-change spectra of electric current change ($I/I_0$) of individual gas sensors. FIG. 9 shows the relationship between gas sensor number (number of gas sensor counted from the gas introduction port of the gas flow path) and the delay time from the gas reaction start time of the first gas sensor (det 1).

Figure 10:
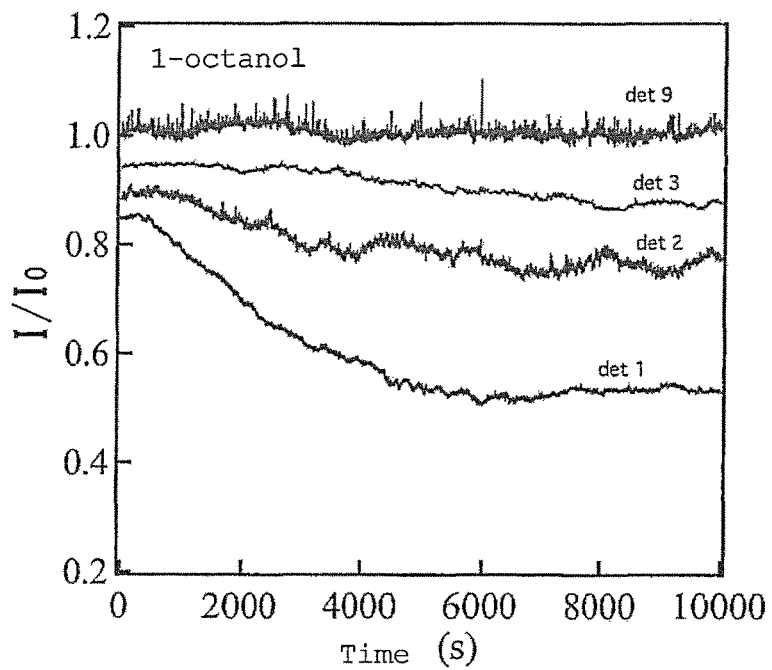
FIG. 10.
Figure 10:
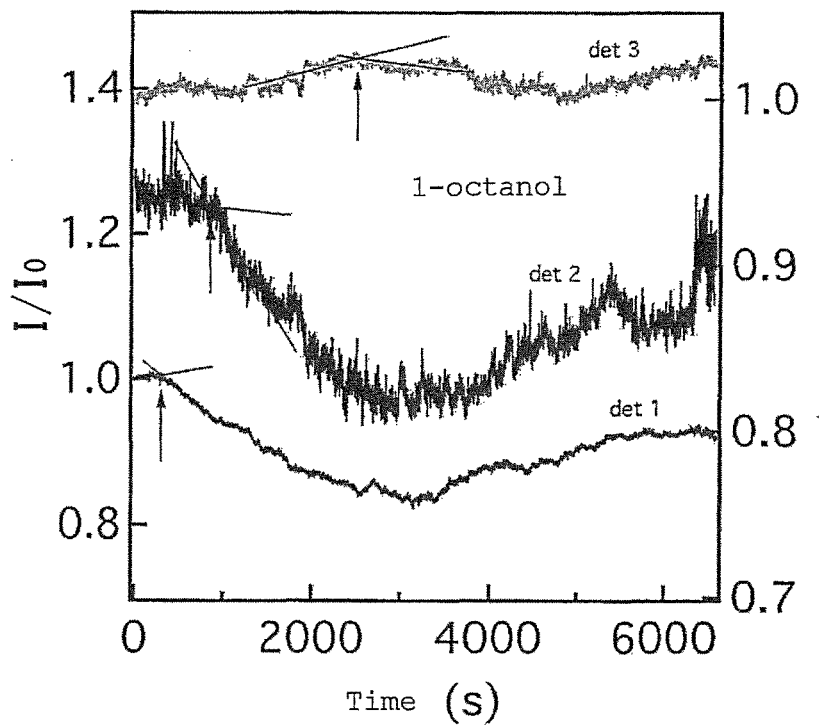

Similarly, FIG. 10(A) and FIG. 10(B) show time-change spectra of electric current change ($I/I_0$) in the first gas sensor (det 1), the second gas sensor (det 2), the third gas sensor (det 3), and the ninth gas sensor (det 9), counting from the gas introduction port 2A of the gas flow path 2, when the gas sensor array 1 having the constitution shown in FIG. 1, wherein 15 gas sensors 3 were provided side by side was used and 1-octanol was flown in the gas flow path 2 as an organic gas. In FIG. 10(A), the horizontal axis shows the elapsed time of test including the time from the start of introduction of a gas into the gas flow path to the completion of the gas introduction, and in FIG. 10(B), the horizontal axis shows the start of introduction of a gas into the gas flow path (0 sec-5000 sec from the start of test). Each spectrum is shown by sliding in the vertical axis direction to avoid superposition.

From FIG. 10(B), it is clear that the time when a decrease in the electric current starts on contact of semiconductor microcrystal with a gas (that is, reaction start time), specified with arrows therein, is delayed in the order of the first gas sensor (det 1), the second gas sensor (det 2), and the third gas sensor (det 3), in the time-change spectra of electric current change ($I/I_0$) of individual gas sensors 3.

In the same manner as above, a delay time in the start of a reaction of time-change spectrum of electric current change ($I/I_0$) between different gas sensors in the gas sensor array was also examined for various organic solvents (1-butanol, ethanol, toluene, benzene, cyclohexane, acetone etc.) other than 1-propanol, methanol, 1-octanol.

Figure 11:
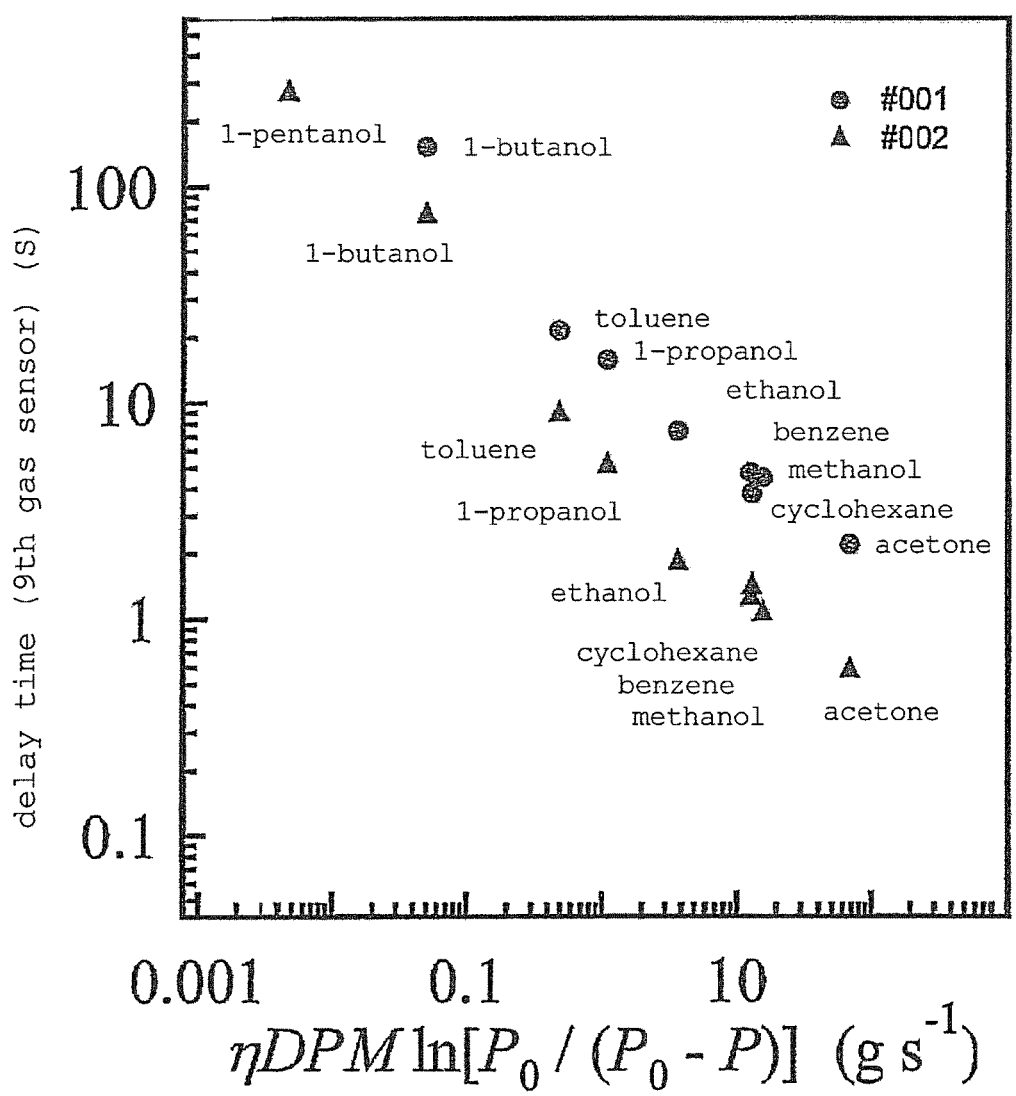
FIG. 11 shows the relationship between a delay time in the start of a reaction of time-change spectrum of electric current change ($I/I_0$) between different gas sensors in the gas sensor array of the present invention, and gas diffusion speed of organic solvents.

FIG. 11 shows the relationship between the delay time of the first gas sensor (det 1) and the ninth gas sensor (det 9), and gas diffusion speed: $\eta DPMln[P_0/(P_0-P)]$ of an organic solvent. The gas diffusion speed ($\eta DPMln[P_0/(P_0-P)]$) is described in the following non-patent documents 4, 5, wherein $\eta$ is a proportionality coefficient, D is a mutual diffusion coefficient of organic solvent gas, P is a vapor pressure, M is a molecular weight and $P_0$ is atmospheric pressure (101.325 kPa). The mutual diffusion coefficient D is calculated from the Fujita formula described in the following non-patent documents 6, 7.

non-patent document 4: J. M. McKelvey and H. E. Hoelscher, Analytical Chemistry, vol. 29, no. 1, p. 123, 1957. "Apparatus for preparation of very dilute gas mixtures", non-patent document 5: A. P. Altshuller and I. R. Cohen, Analytical Chemistry 1960 32 (7), pp 802-810. "Application of Diffusion Cells to Production of Known Concentration of Gaseous Hydrocarbons.", non-patent document 6: Shigefumi Fujita, Chemical Engineering 28(3), 251-52(1964), non-patent document 7: Society of Chemical Engineers, Japan, "Chemical Engineering Handbook, Revised 4th ed.", Maruzen, Tokyo, 1978, p. 10.

In FIG. 11, the plot #001 shows the results when an accumulation layer of semiconductor crystal was formed using a 1.2 mm-width carbon tape for a 1.0 mm-width band-like first electrode (copper foil electrode), and the plot #002 shows the results when an accumulation layer of semiconductor crystal was formed using a 1.1 mm-width carbon tape for a 1.0 mm-width band-like first electrode (copper foil electrode).

From FIG. 11, it is clear that, when sensing of an organic gas is performed by the gas sensor array of the present invention, time-change spectrum of electric current change ($I/I_0$) that occurs in each of the plural gas sensors shows a delay between different gas sensors, and a specific delay time is shown for each organic gas. Therefore, the gas type of the organic gas can be distinguished by measuring the delay time. In FIG. 11, the plot #001 shows the results when the gas sensor is one wherein an accumulation layer of semiconductor crystal is formed using a 1.2 mm-width carbon tape (conductive double-sided tape) for a 1.0 mm-width band-like first electrode (copper foil electrode), and the plot #002 shows the results when the gas sensor is one wherein an accumulation layer of semiconductor crystal was formed using a 1.1 mm-width carbon tape (copper foil electrode) for a 1.0 mm-width band-like first electrode (copper foil electrode). When a 1.2 mm-width carbon tape (conductive double-sided tape) is used, the gas flow rate is faster than by using a 1.1 mm-width carbon tape (conductive double-sided tape). This is assumed to be because the change of the width of the carbon tape (conductive double-sided tape) substantially changes the width of the gas flow path, which in turn changes the gas flow rate in the gas flow path (Bernoulli's theory). Therefore, since the above-mentioned delay time can be adjusted by changing the design width of gas flow path, or substantial change of the width of the gas flow path by the size change of constituent members of the gas sensor array, it is clear that the time for determination of the gas type (sensing time) by a gas sensor array can be adjusted.

The time-change spectrum of electric current change that occurs in each gas sensor of the plural gas sensors in the gas sensor array of the present invention shows a delay, between different gas sensors, not only in the aforementioned reaction start time, which is the time when the electric current starts to decrease due to the contact of the semiconductor microcrystal and gas, but also in the peak time when the amount of electric current decrease ($\Delta I$) becomes maximum and relaxation time after reaction, and a specific delay time is shown for each organic gas. Therefore, the gas type of the organic gas can also be distinguished by measuring a delay time of the peak time or the relaxation time in the time-change spectrum.

In the gas sensor array of the present invention, the number, size and the like of the gas sensor are not particularly limited. In the case of a gas sensor array 1 having the constitution of FIG. 1, the number of the plural gas sensors 3 is preferably about 2-15. The width of the second electrode 5 (W1 in FIG. 2(A)) is preferably about 0.1-1.5 mm. The SN ratio is degraded as the width becomes smaller, but response to the reaction tends to become faster. The SN ratio is improved as the width becomes larger, but response to the reaction tends to become slower. The clearance between adjacent gas sensors 3 (that is, clearance between adjacent second electrodes 5 (W2 in FIG. 2(A)) is preferably about 0.1-0.5 mm. When the distance is too small, the difference in the time-change spectrum of electric current change between adjacent gas sensors tends to be not remarkable, and when the distance is too large, the difference in the time-change spectrum of electric current change between adjacent gas sensors becomes remarkable, but signal intensity (level of electric current change) tends to be suddenly small.

The delay time in time-change spectrum of electric current change ($I/I_0$) between different gas sensors in the gas sensor array of the present invention is basically determined by measuring a delay time in time-change spectrum of electric current change ($I/I_0$) of a gas sensor by using, as a standard, the time-change spectrum of electric current change ($I/I_0$) of the gas sensor closest to the gas introduction port of the gas flow path. However, the method is not limited thereto. The delay time may be determined by comparing time-change spectra of electric current change of two gas sensors that clearly show a specific delay time for each gas, from the plural gas sensors provided side by side along the gas flowing direction of the gas flow path.

The delay time may be measured by additionally setting a monitor that displays time-change spectrum of electric current change ($I/I_0$) of individual gas sensor 3 on the gas sensor array and measuring on the monitor, or by a microcomputer that automatically calculates same from an electric output value of the sensor response (S) of the gas sensor.

It is clear that, when sensing of an organic gas is performed by the gas sensor array of the present invention, time-change spectrum of electric current change ($I/I_0$) that occurs in each gas sensor of the plural gas sensors shows a delay between different gas sensors, and a specific delay time is shown for each organic gas. Therefore, the gas type of the organic gas can be distinguished by measuring the delay time. For a gas type showing a long delay time (e.g., 1-octanol), the first gas sensor (det 1) and a small-numbered gas sensor (e.g., the second gas sensor (det 2)) at a position comparatively close to the first gas sensor (det 1) may be used. By forcively accelerating the gas flow rate by using the below-mentioned gas flow method, the delay time can also be measured by a detector having a comparatively large gas sensor number. On the other hand, for a gas type showing a short delay time (e.g., acetone), the first gas sensor (det 1) and a large-numbered gas sensor (e.g., the ninth gas sensor (det 9) or thereafter) at a position comparatively far from the first gas sensor (det 1) may be used.

In addition, a gas analysis system automatically distinguishing a gas type can be produced by, for example, previously forming a database containing the data of the relationship between a delay time of a gas sensor having a particular location number shown in FIG. 11 and a gas diffusion speed of an organic solvent and the like, and additionally setting the database and a calculation part that determines the gas type of a gas to be analyzed based on the comparison results of the delay time detected by a gas sensor array and the data preserved in the database on a gas sensor array.

While a method of identifying (distinguishing) a gas type of a gas to be analyzed from a delay time between different sensors in time-change spectrum of electric current change ($I/I_0$) is explained above, the gas sensor array of the present invention can identify the component ratio of a gas to be analyzed composed of a mixed gas.

Figure 12:
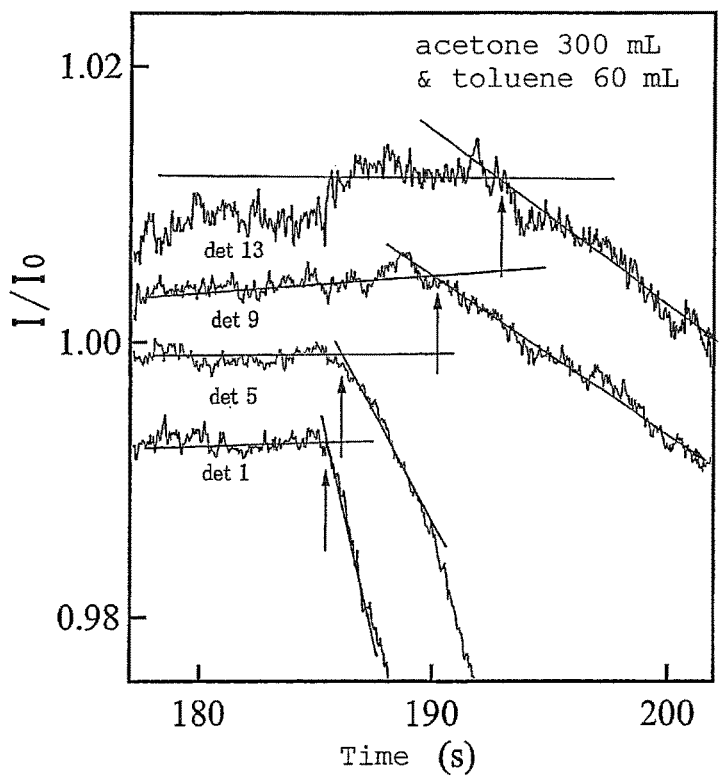
FIG. 12.
Figure 12:
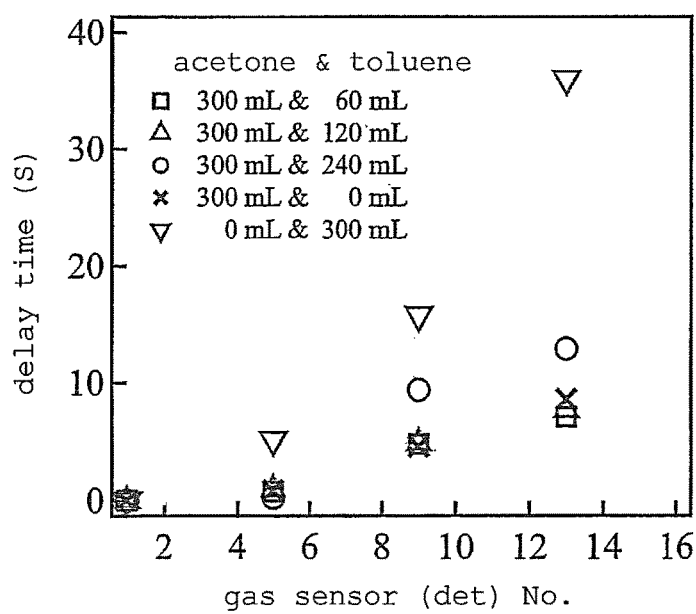

FIG. 12 shows the measurement results of a delay time between different sensors in time-change spectrum of electric current change that occurs in each gas sensor 3 when the gas sensor array 1 having the constitution shown in FIG. 1, which was obtained in the below-mentioned Experimental Example, was used and a mixed gas with varying mixing ratio of acetone and toluene was flown in the gas flow path 2. FIG. 12(A) shows time-change spectra of electric current change in the first gas sensor (det 1), the fifth gas sensor (det 5), the ninth gas sensor (det 9) and the thirteenth gas sensor (det 13), counting from the gas introduction port 2A of the gas flow path 2, when a mixed gas of acetone (300 mL) and toluene (60 mL) was flown. Similarly, a mixed gas of acetone (300 mL) and toluene (120 mL), a mixed gas of acetone (300 mL) and toluene (240 mL), single acetone gas (300 mL), single toluene gas (300 mL) were used, time-change spectrum of electric current change in the first gas sensor (det 1), the fifth gas sensor (det 5), the ninth gas sensor (det 9), and the thirteenth gas sensor (det 13) is measured and, from those results, a delay time between the first gas sensor (det 1) and the fifth gas sensor (det 5), a delay time between the first gas sensor (det 1) and the ninth gas sensor (det 9), and a delay time between the first gas sensor (det 1) and the thirteenth gas sensor (det 13) are summarized in FIG. 12(B). In FIG. 12(A), each spectrum is shown by sliding in the vertical axis direction to avoid superposition.

From FIG. 12(B), it is clear that when a gas has a low toluene concentration, irrespective of the component ratio of toluene and acetone, both a gas sensor (det 5) near the gas introduction port 2A of the gas flow path 2 and a gas sensor (det 9) far from the gas introduction port 2A show almost the same delay time in time-change spectrum of electric current change as that in the first gas sensor (det 1), when a gas has a high toluene concentration, a delay time in time-change spectrum of electric current change relative to the first gas sensor (det 1) is approximately the same in a gas sensor (det 5) near the gas introduction port 2A of the gas flow path 2 irrespective of the component ratio of toluene and acetone and, in gas sensors (det 9, det 13) far from the gas introduction port 2A of the gas flow path 2, an influence of toluene on a delay time in time-change spectrum of electric current change in the first gas sensor (det 1) becomes high, and the delay time becomes different from that of a gas having a low toluene concentration.

Therefore, using the gas sensor array of the present invention, the component ratio of the mixed gas can be specified from the delay time between different sensors in a time-change spectrum of electric current change that occurs in each gas sensor of plural gas sensors, by flowing the mixed gas in the gas flow path.

Figure 13:
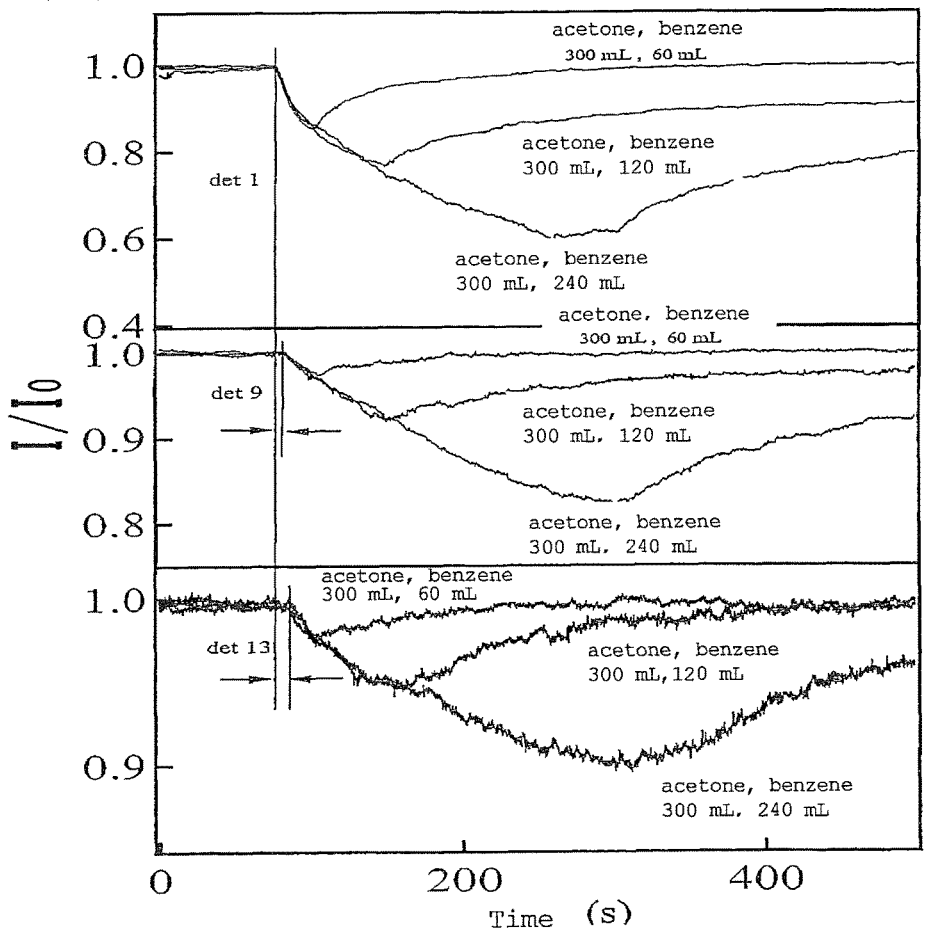
FIG. 13.
Figure 13:
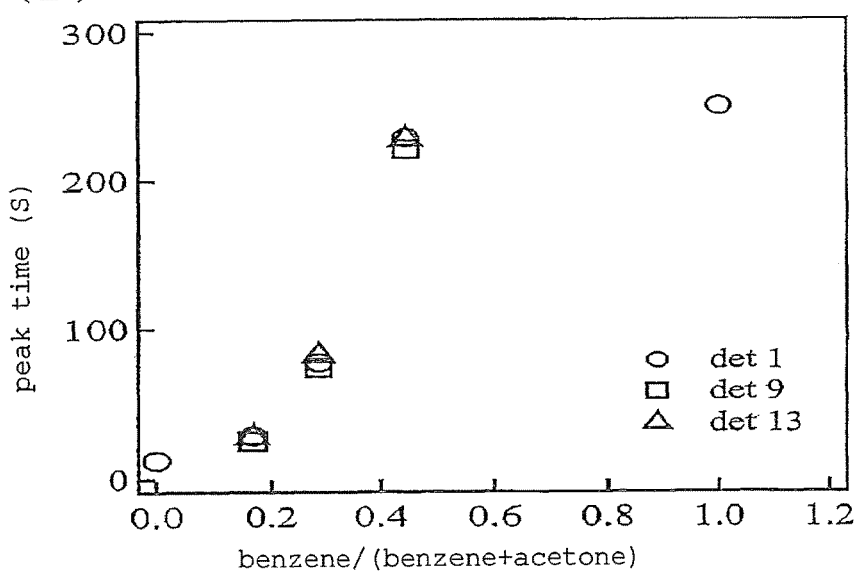

FIG. 13(A) shows time-change spectra of electric current change in the first gas sensor (det 1), the ninth gas sensor (det 9) and the thirteenth gas sensor (det 13) when the gas sensor array 1 having the constitution shown in FIG. 1, which was obtained in the below-mentioned Experimental Example, was used and a mixed gas with varying mixing ratio of acetone and benzene was flown in the gas flow path 2. With a mixed gas of acetone and benzene, the electric current change start time is different in each sensor in this time scale. However, a difference in the start time due to the ratio of benzene in the mixed gas is not visible since an influence of acetone appears strongly. FIG. 13(B) shows the ratio of benzene in a mixed gas, and a peak arrival time in time-change spectrum of electric current change in the first gas sensor (det 1), the ninth gas sensor (det 9), and the thirteenth gas sensor (det 13). It is clear from FIG. 13(B) that the peak arrival time in the time-change spectrum of electric current change clearly differs in a gas sensor at a particular position depending on the component ratio of a mixed gas.

Therefore, using the gas sensor array of the present invention, the gas components of a gas to be analyzed, which is a mixed gas can be specified from the comparison of the peak arrival time in a time-change spectrum of electric current change that occurs in each gas sensor of plural gas sensors, by flowing the mixed gas in the gas flow path.

Figure 14:
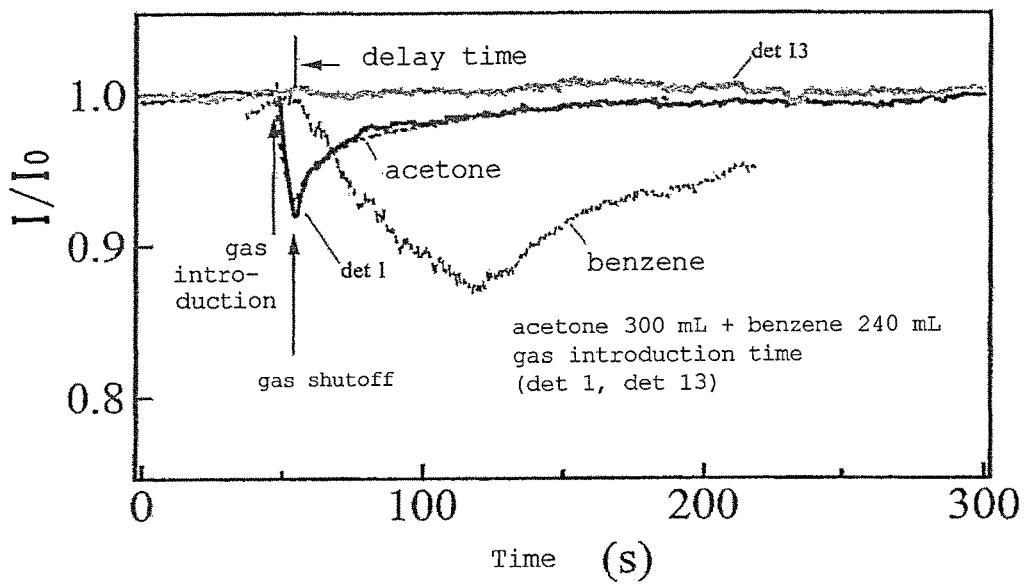
FIG. 14 shows time-change spectra of electric current change in the first gas sensor and the thirteenth gas sensor, which are counted from the gas introduction port, when a mixed gas of acetone and benzene is flown in the gas flow path in the gas sensor array of the present invention for a short time (FIG. 14(A)), and time-change spectra of electric current change in the first gas sensor and the thirteenth gas sensor when flown for a long time (FIG. 14(B)). The inserted figure in FIG. 14(B) is an enlarged view wherein a gas introduction start time into the gas flow path in FIG. 14(B) is the horizontal axis.
Figure 14:
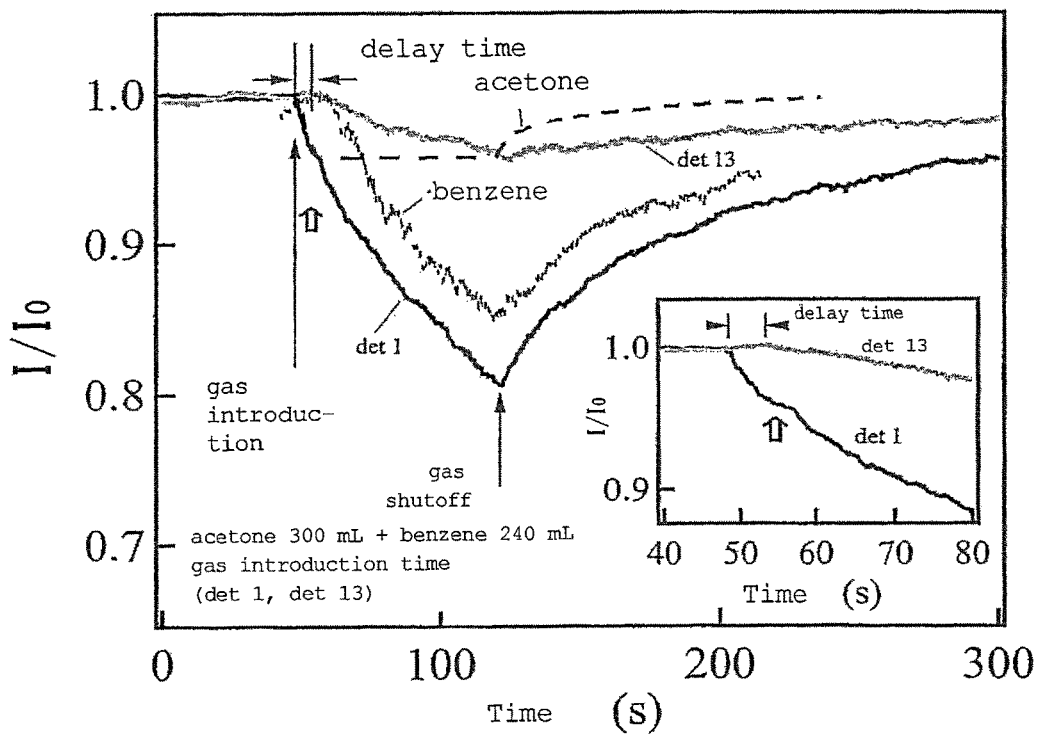

FIG. 14(A) shows time-change spectrum of electric current change (solid line affixed with det 1 in the Figure) in the first gas sensor and time-change spectrum of electric current change (solid line affixed with det 13 in the Figure) in the thirteenth gas sensor, when the gas sensor array 1 having the constitution shown in FIG. 1, which was obtained in the below-mentioned Experimental Example, was used and a mixed gas of acetone and benzene was flown in the gas flow path 2 for 7.0 second. FIG. 14(B) shows time-change spectrum of electric current change (solid line affixed with det 1 in the Figure) in the first gas sensor and time-change spectrum of electric current change (solid line affixed with det 13 in the Figure) in the thirteenth gas sensor, when the gas sensor array 1 having the constitution shown in FIG. 1, which was obtained in the below-mentioned Experimental Example, was used and a mixed gas of acetone and benzene was flown in the gas flow path 2 for 74.0 seconds. For comparison, FIG. 14(A) and FIG. 14(B) respectively show time-change spectrum of electric current change measured by the first gas sensor (det 1) (wavy line affixed with "acetone") when acetone alone was flown in the gas flow path 2, and time-change spectrum of electric current change measured by the first gas sensor (det 1) (wavy line affixed with "benzene") when benzene alone was flown in the gas flow path 2.

As shown in FIG. 14(A), when a mixed gas of acetone and benzene flows in a gas flow path for a short time, the contact time of semiconductor microcrystal and the gas in a gas sensor becomes short. As a result, the time-change spectrum of electric current change of the mixed gas overlaps with the time-change spectrum of electric current change of acetone alone in the first gas sensor (det 1) near the introduction port of the gas flow path, due to which acetone alone is detected (benzene is not detected). Semiconductor microcrystal shows rapid reaction and recovery with acetone, and benzene shows electric current change (spectrum change) in the thirteenth gas sensor (det 13) far from the introduction port of the gas flow path, which is due to a short contact time with semiconductor microcrystal.

On the other hand, as shown in FIG. 14(B), when a mixed gas flows in a gas flow path for a long time, the contact time of semiconductor microcrystal and the gas in a gas sensor becomes long. As a result, acetone and benzene are detected by the first gas sensor (det 1) near the introduction port of the gas flow path (solid line affixed with det1 in Figure), and benzene with large signals is mainly detected by the thirteenth gas sensor (det 13) far from the introduction port of the gas flow path (solid line affixed with det13 in Figure). The inserted figure in FIG. 14(B) is an enlarged view wherein the gas introduction start time is the horizontal axis, and it is observed that acetone is mainly detected from the spectrum near gas introduction start time into the gas flow path (blank arrow in Figure).

Therefore, using the gas sensor array of the present invention, the gas component of a gas to be analyzed composed of a mixed gas can be specified by flowing a gas to be analyzed in the gas flow path while applying a constant voltage to plural gas sensors under plural conditions of different flowing time of the gas to be analyzed in the gas flow path, observing time-change spectra of electric current change in plural gas sensors under plural conditions, and comparing the time-change spectra obtained under the plural conditions.

Figure 15:
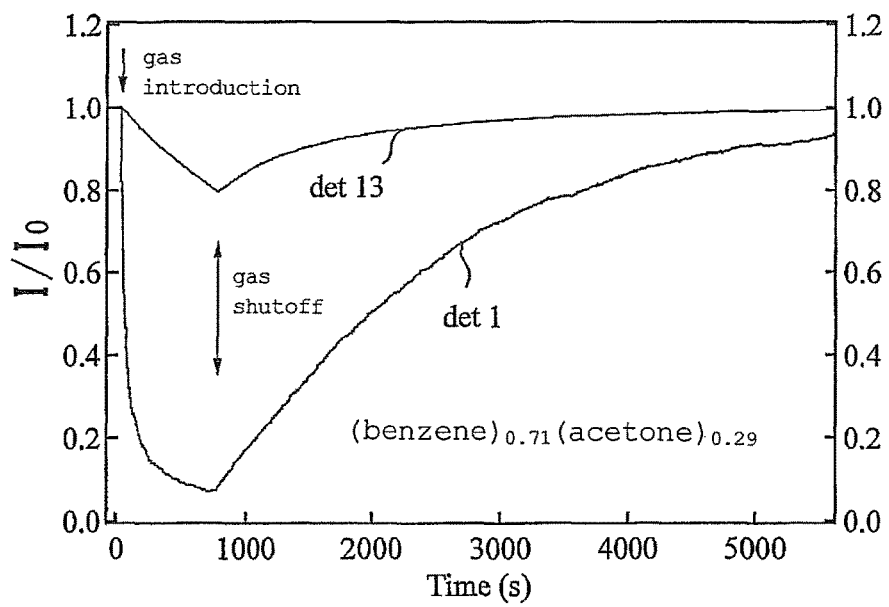
FIG. 15.
Figure 15:
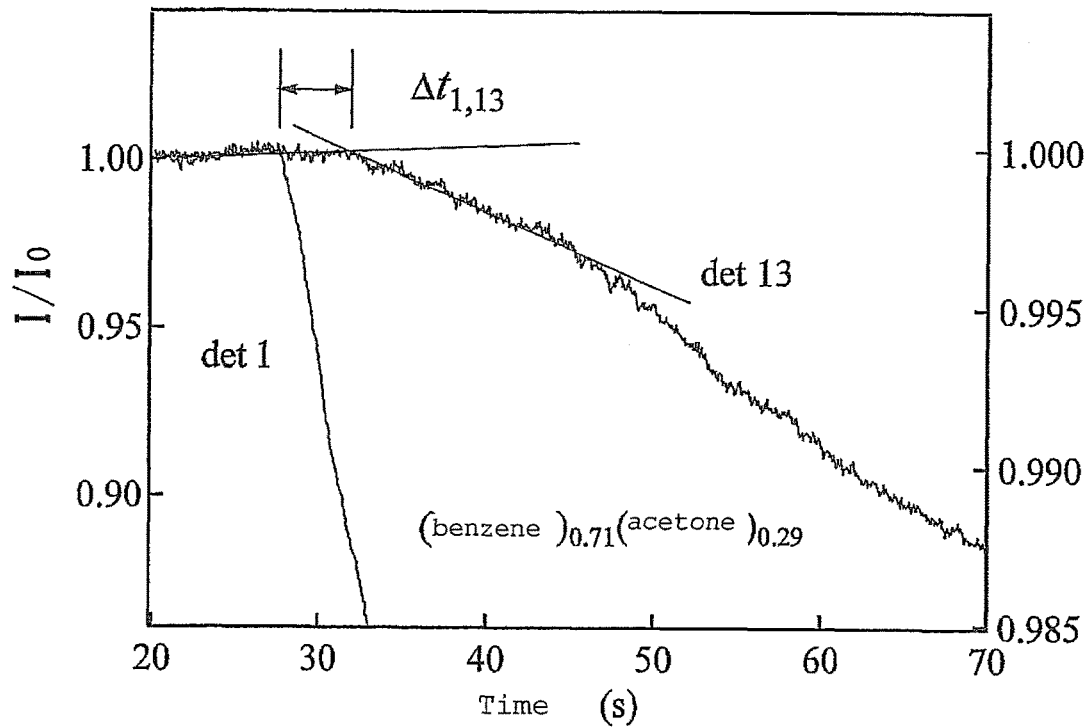
Figure 16:
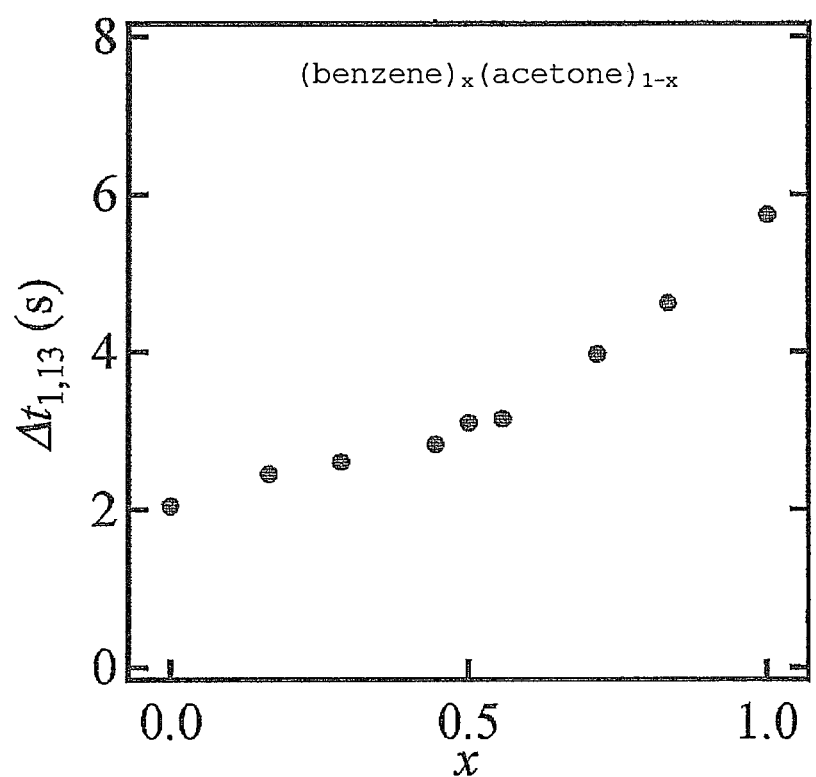
FIG. 16 shows the relationship with the delay time difference ($\Delta t_{1,13}$) of the first gas sensor (det 1) and the thirteenth gas sensor (det 13) when a mixed gas of acetone and benzene is flown in the gas sensor array of the present invention.

FIG. 15(A) shows time-change spectrum of electric current change in the first gas sensor (det 1) and the thirteenth gas sensor (det 13), when the gas sensor array 1 having the constitution shown in FIG. 1 (having a gold-plated electrode surface), which was obtained in the below-mentioned Experimental Example, was used and a mixed gas of acetone and benzene at a mixing ratio (benzene/acetone) of 0.71/0.29 was flown in the gas flow path 2. FIG. 15(B) is an enlarged view when 20 sec-70 sec passed from the start of the measurement in FIG. 15(A). It is clear that when introduction of gas is started at 28 sec, the first gas sensor (det 1) and 4.2 seconds of delay time difference ($\Delta t_{1,13}$) of the thirteenth gas sensor (det 13) lapsed, time-change spectrum of electric current change of the thirteenth gas sensor appears. FIG. 16 shows the relationship between the component ratio of a mixed gas of acetone and benzene and the delay time difference ($\Delta t_{1,13}$) of the first gas sensor (det 1) and the thirteenth gas sensor (det 13). The delay time difference ($\Delta t_{1,13}$) is a difference between the time when the electric current starts to decrease upon contact with a gas in the first gas sensor (det 1) (reaction start time) and the time when the electric current starts to decrease upon contact with a gas in the thirteenth gas sensor (det 13) (reaction start time).

From the comparison of FIG. 15(B) and FIG. 14(B), it is clear that improved data of Signal-to-Noise Ratio (SN ratio) is obtained by plating an electrode surface of the opposing electrode (upper electrode, lower electrode) of the gas sensor with gold. From FIG. 16, it is clear that when the gas component of the measurement target (gas to be analyzed) has been clarified (that is, when the gas to be analyzed has been clarified to be a mixed gas of benzene and acetone), the component ratio of the gas components (component ratio of benzene and acetone) of the gas to be analyzed can be specified from the measurement data of difference in the delay time of reaction start time between different gas sensors of a gas sensor array.

Figure 17:
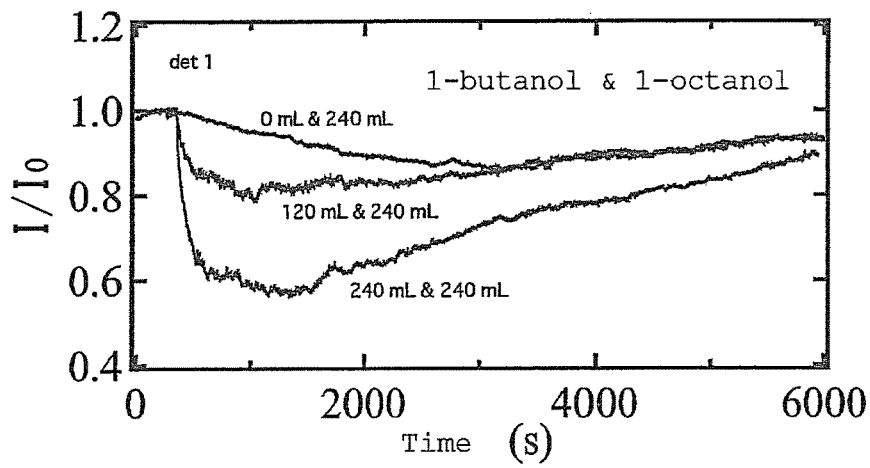
FIG. 17.
Figure 17:
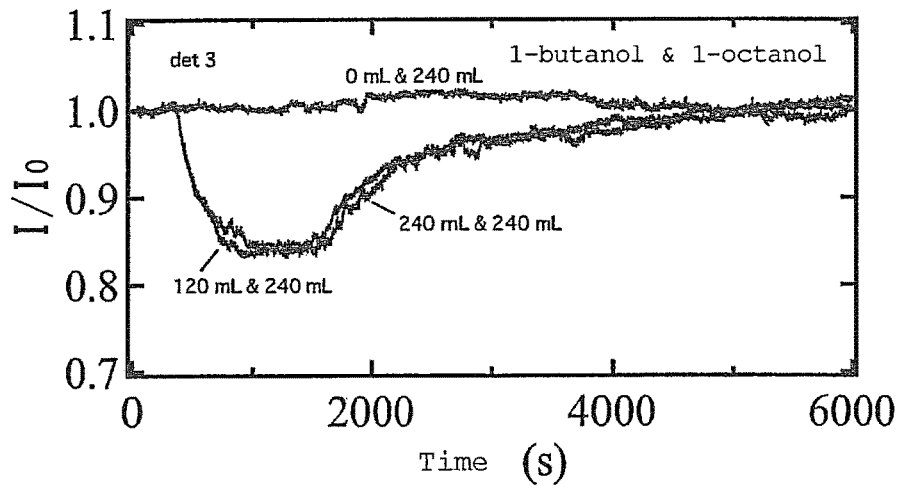
Figure 17:
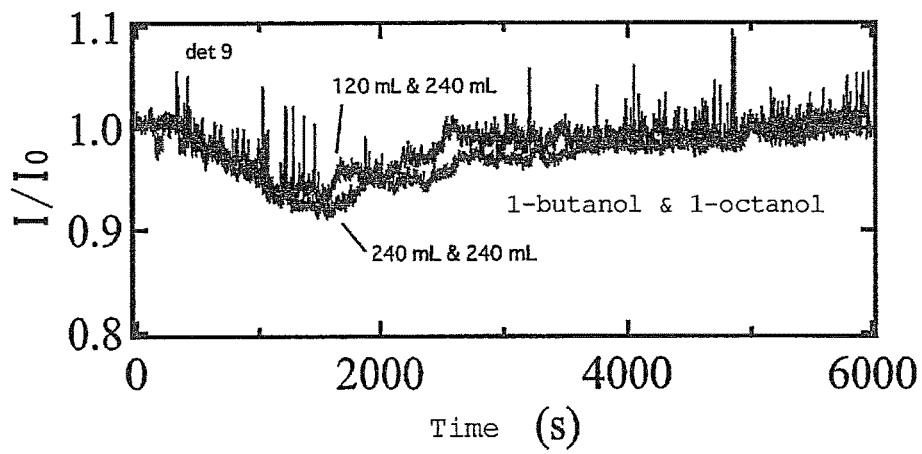

FIG. 17 shows time-change spectrum of electric current change in the first gas sensor (det 1) (FIG. 17(A)), time-change spectrum of electric current change in the third gas sensor (det 3) (FIG. 17(B)) and time-change spectrum of electric current change in the ninth gas sensor (det 9) (FIG. 17(C)), when the gas sensor array 1 having the constitution shown in FIG. 1, which was obtained in the below-mentioned Experimental Example, was used and a mixed gas of 1-butanol and 1-octanol at varying mixing ratio was flown in the gas flow path 2. For comparison, FIG. 17(A) and FIG. 17(B) show time-change spectra of electric current change when 1-octanol alone was flown in the gas flow path 2.

From FIG. 17(A)-FIG. 17(C), when 1-octanol alone was flown, the time-change spectrum of electric current change reaches peak near 3200 seconds in the first gas sensor (det 1), after which overlaps with time-change spectrum of electric current change of a mixture of 1-butanol and 1-octanol. In the third gas sensor (det 3), when 1-octanol alone was flown, the time-change spectrum of electric current change starts to appear near 2500 seconds, reaches peak near 4800 seconds, after which overlaps with time-change spectrum of electric current change of a mixture of 1-butanol and 1-octanol. This means that this time zone shows time-change spectrum of electric current change of 1-octanol alone. In a mixed gas of 1-butanol and 1-octanol, therefore, since time-change of electric current change by 1-butanol is faster than time-change of electric current change by 1-octanol in individual gas sensors, electric current change is based on 1-butanol in an early stage of time-change spectrum of electric current change, and the electric current change by 1-octanol is not reflected. An influence of 1-octanol appears in a considerably late time zone (3200 seconds or after).

Figure 18:
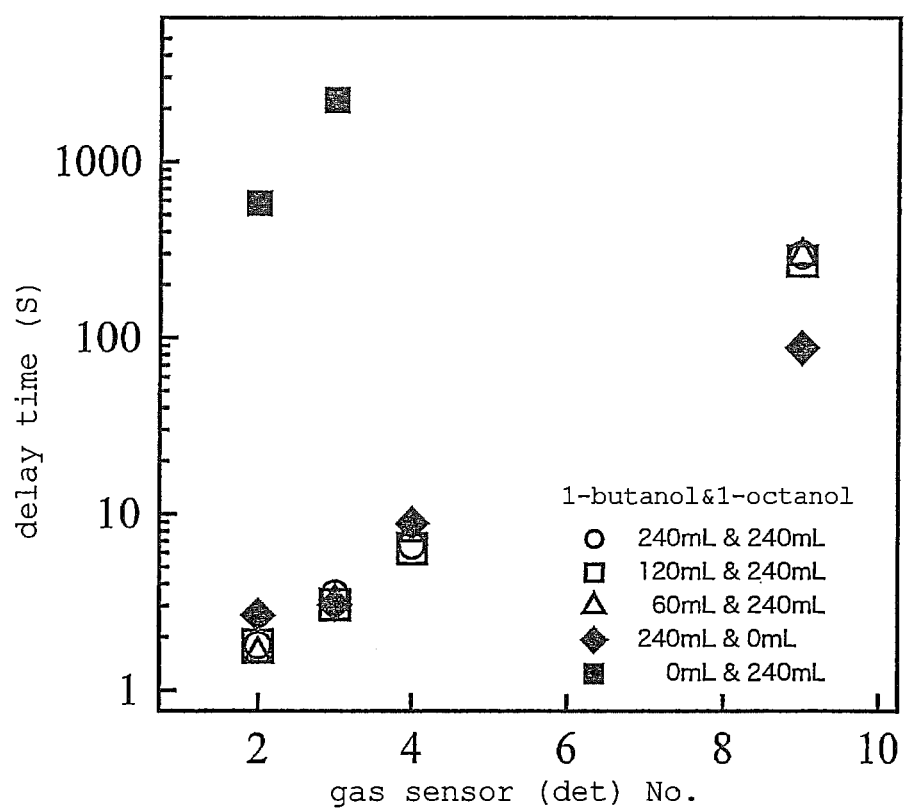
FIG. 18 shows time-change spectrum of electric current change of the first gas sensor (det 1), counted from the gas introduction port, and a delay time (delay time in gas reaction start time) in time-change spectra of electric current change of other gas sensors (the second gas sensor (det 2), the third gas sensor (det 3) and the fourth gas sensor (det 4)), when a mixed gas of 1-butanol and 1-octanol having a varying mixing ratio is flown in the gas sensor array of the present invention.

FIG. 18 shows a delay time of gas reaction start time in the time-change spectra of electric current change of the second gas sensor (det 2), the third gas sensor (det 3), the fourth gas sensor (det 4), and the ninth gas sensor (det 9) from the time-change spectrum of electric current change of the first gas sensor, when a mixed gas of 1-butanol and 1-octanol having varying mixing ratio is flown in the gas flow path 2. For comparison, the delay time when 1-butanol alone was flown in the gas flow path 2 and when 1-octanol alone was flown in the gas flow path 2 is also shown. From FIG. 18, it is clear that the delay time by the mixed gas is the same as that by 1-butanol alone from the second gas sensor (det 2) to the fourth gas sensor (det 4).

Therefore, using the gas sensor array of the present invention, 1-butanol which is a gas component showing rapid time-change of electric current change (that is, gas component showing spectrum that changes sharply in a short time) can be separated and detected instantaneously even from a mixed gas of 1-butanol (number 4 in FIG. 6) and 1-octanol (number 8 in FIG. 6) having almost the same value of detection sensitivity (sensor response S) in the gas sensor of FIG. 6. 1-Octanol, which is a gas component showing slow time-change of electric current change, can be specified by component analysis by spectrum at 3200 seconds or thereafter.

Figure 19:
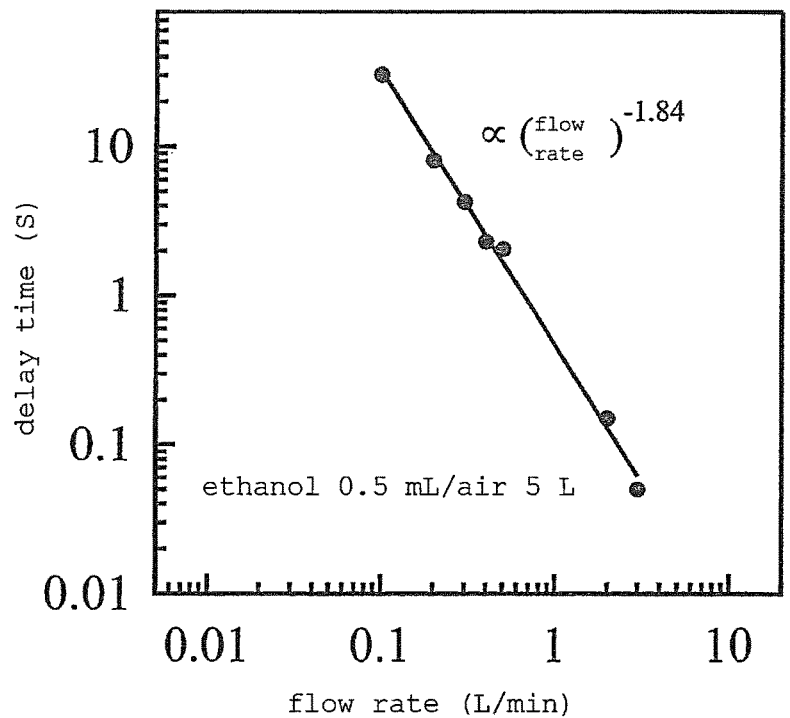
FIG. 19 shows the measurement results of a delay time in time-change spectrum of electric current change, which occurs between the first gas sensor (det 1) and the thirteenth gas sensor (det 13), which are counted from the gas introduction port, when ethanol gas is introduced at a varying flow rate into the gas flow path in the gas sensor array of the present invention.

FIG. 19 shows the measurement results of a delay time in time-change spectrum of electric current change between the first gas sensor (det 1) and the ninth gas sensor (det 9), when the gas sensor array 1 having the constitution shown in FIG. 1, which was obtained in the below-mentioned Experimental Example, was used and ethanol gas at a varying flow rate was introduced into a gas flow path. The results reveal that a delay time in time-change spectrum of electric current change between different gas sensors of a gas sensor array is proportional to the 1/1.84 power of the flow rate of a gas (heading toward a gas sensor array). Therefrom it is clear that a delay time in time-change spectrum of electric current change between different gas sensors of a gas sensor array becomes larger as the flow rate of a gas heading toward a gas sensor array becomes slower.

Figure 20:
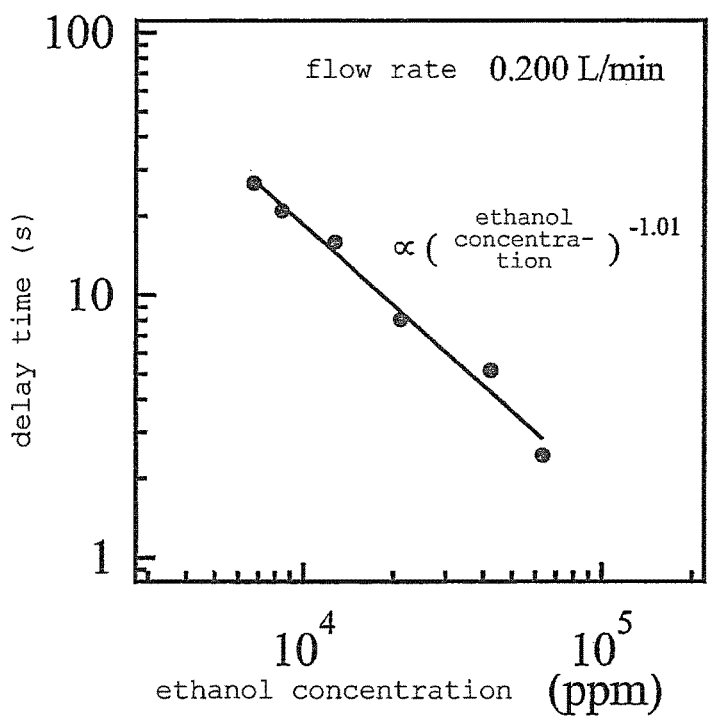
FIG. 20 shows the measurement results of a delay time in time-change spectrum of electric current change, which occurs between the first gas sensor (det 1) and the ninth gas sensor (det 9), which are counted from the gas introduction port, when ethanol gas is introduced at a varying concentration into the gas flow path in the gas sensor array of the present invention.

FIG. 20 shows the measurement results of a delay time in time-change spectrum of electric current change between the first gas sensor (det 1) and the ninth gas sensor (det 9), when the gas sensor array 1 of FIG. 1, which was obtained in the below-mentioned Experimental Example, was used and ethanol gas having a varying concentration was introduced into a gas flow path at a constant flow rate. The results reveal that a delay time in time-change spectrum of electric current change between different gas sensors of a gas sensor array is proportional to the inverse number of the concentration of a gas heading toward a gas sensor array. Therefrom it is clear that a delay time in time-change spectrum of electric current change between different gas sensors of a gas sensor array becomes shorter as the concentration of a gas heading toward a gas sensor array becomes slower.

Figure 21:
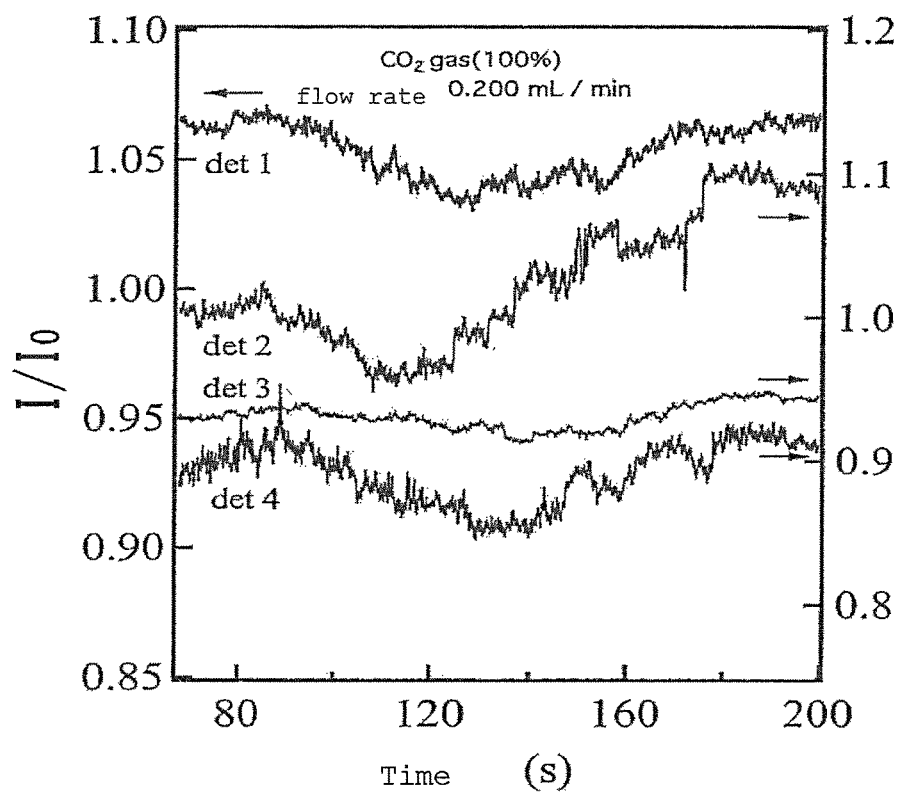
FIG. 21.
Figure 21:
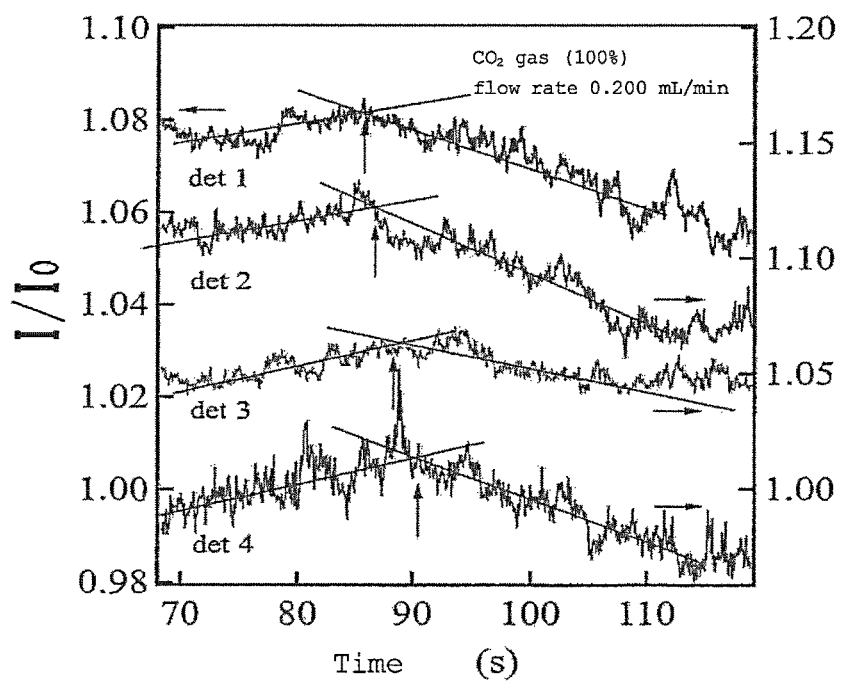

The foregoing is an explanation by referring to a case when a gas to be analyzed is an organic gas. FIG. 21 shows time-change spectra of electric current change in the first gas sensor (det 1), the second gas sensor (det 2), the third gas sensor (det 3), and the fourth gas sensor (det 4), counting from the gas introduction port 2A of the gas flow path 2.

FIG. 21(A) uses up to 200 seconds from the start of gas introduction into a gas flow path as the horizontal axis, and FIG. 21(B) uses up to 120 seconds from the start of gas introduction into a gas flow path as the horizontal axis. FIG. 18 reveals that the gas sensor array of the present invention is capable of gas detection (determination of gas) even of an inorganic gas, since a delay in the time-change spectrum of electric current change ($I/I_0$) between different gas sensors occurs even with carbon dioxide gas.

In the gas sensor array of the present invention, when selenium nanowire is used as a semiconductor microcrystal of gas sensor 3, the thinner the size (D) of selenium nanowire, the larger the amount of decrease in the electric current (sensitivity) of a sensor tends to be upon contact with an organic gas. Therefore, the thickness (D) of the selenium nanowire is preferably not more than 500 nm, more preferably not more than 300 nm. While the lower limit is not particularly limited, it is preferably not less than several nm. On the other hand, the length (L) of the selenium nanowire is longer the better so that the wire will overlap. Therefore, the aspect ratio (L/D) is preferably not less than 5, more preferably not less than 10, particularly preferably not less than 15. While the upper limit is not particularly limited, it is preferably not more than 50, more preferably not more than 30.

The thickness (D) and length (L) of the selenium nanowire in the present invention are obtained by taking an SEM photograph, measuring the thickness and length of plural selenium nanowires (sample number: 50) from the photograph image, and selecting the peak values of distribution in each distribution graph.

In the gas sensor array of the present invention, when microcrystalline selenium composed of monoclinic polyhedron is used as a semiconductor microcrystal of gas sensor 3, an average particle size thereof is preferably 1-10 µm. The average particle size is obtained by taking an SEM photograph, measuring the particle size of plural particles (sample number: 50) from the photograph image, and selecting the peak value of distribution in the distribution graph obtained therefrom.

The gas sensor array of the present invention is particularly preferable for the determination of gas type, specification of gas components of a mixed gas, specification of the component ratio of a mixed gas and the like in organic gas. The organic gas in the present invention is a volatile organic compound whose influence on the environment and human body is concerned. Examples thereof include methane, ethane, n-butane, isobutane, 2,2-dimethylbutane, 2,3-dimethylbutane, n-pentane, 2-methylpentane, 2,4-dimethylpentane, n-hexane, 3-methylhexane, n-heptane, 3-methylheptane, nonane, decane, undecane, methylcyclopentane, cyclohexane, methylcyclohexane, ethylcyclohexane, bicyclohexyl, propylene, cis-2-butene, trans-2-butene, 2-methyl-2-butene, 2-methyl-1-butene, 1,3-butadiene, isoprene, cis-2-pentene, trans-2-pentene, 1-heptene, dipentene, benzene, toluene, xylene, 1,3,5-trimethylbenzene, ethylbenzene, cumene, styrene, naphthalene, tetralin, chloromethane, dichloromethane, chloroform, methyl bromide, chloroethane, 1,2-dichloroethane, trichloroethane, trichloroethylene, tetrachloroethylene, tetrafluoroethylene, vinyl chloride, 1,1-dichloroethylene, n-propylbromide, 1,2-dichloropropane, allyl chloride, chlorobenzene, o-dichlorobenzene, methanol, ethanol, isopropanol, n-butanol, isobutanol, ethylene glycol, benzyl alcohol, phenol, methylmercaptan, ethylmercaptan, ethylene glycol monomethylether, ethylcellosolve, isopropylcellosolve, butylcellosolve, propylene glycol monomethylether, propylene oxide, ethylene oxide, epichlorohydrin, tetrahydrofuran, 1,4-dioxane, formic acid methyl, ethyl acetate, trifluoroethyl acetate, propyl acetate, butyl acetate, vinyl acetate, methyl Cellosolve acetate, ethyl Cellosolve acetate, propylene glycol monomethyl ether acetate, propionic acid, acrylic acid, methyl acrylate, methyl methacrylate, acetone, methyl ethyl ketone, methyl isopropyl ketone, methyl isobutyl ketone, methyl n-butyl ketone, methyl amyl ketone, cyclopentanone, cyclohexanone, isophorone, dimethyl sulfoxide, trimethylamine, triethylamine, cyclohexylamine, pyridine, piperidine, formaldehyde, acetaldehyde, acetonitrile, acrylonitrile, N,N-dimethylformamide, N-methyl-2-pyrrolidone, trifluoro methyl propyl ketone and the like.

The gas sensor array of the present invention can also deal with inorganic gas, and examples of the inorganic gas include carbon dioxide, carbon monoxide, nitric oxide, nitric dioxide, carbon disulfide, ammonia and the like.

In the gas sensor array of the present invention, the electric output values (delay time, peak time, spectrum shape etc.) based on the time-change spectrum of electric current change that occurs in each gas sensor show specific values for each gas when a gas to be analyzed is flown in a gas flow path while applying a constant voltage to plural gas sensors. Therefore, an automatic gas analysis system can be constituted by forming a gas detection map of each gas in advance, which correlates such values with the property values of the gas, as a database, and additionally setting a calculation part that specifies gas type, component ratio of a mixed gas or gas component of a mixed gas by utilizing the database, on a gas sensor array.

One embodiment of the determination method of the gas type, component ratio of the mixed gas and the like by an automatic measurement program for an automatic gas analysis system is shown below.

[I] Determination of Reaction Start Time of Each Sensor by Contact with Gas in Gas Sensor Array, and Measurement of Gas Type and Mixed Gas Component Ratio and the Like 1. Determination of Initial Electric Current Value $I_0$ Before Contact with Gas:

To reduce time variation due to the noise of the electric current that flows in the $k^{th}$ sensor det k before contact with a gas, an average time $<I_{k,0}>$ of the electric current value that flows in the sensor is determined.

2. Determination of the Presence or Absence of Decrease in Electric Current Value Due to Contact with Gas:

The kth sensor det k reacts on contact with a gas, and the electric current value $I_k$ that flows in this sensor starts to decrease from $<I_{k,0}>$. At this time, the electric current value $I_{k,j}(t_{k,j})$ at measurement time $t_{k,j}$ is measured, $[I_{k,j}(t_{k,j})-<I_{k,0}>]$ is calculated, plus and minus is determined, and the number of minus $n_k$ is determined. This value is compared with the upper limit value $N_k$ of the number of minus relative to the kth sensor det k and whether it reaches $N_k$ is determined.

3. Determination of Reaction Start Time by Contact with Gas:

In the kth sensor det k, when $N_k$ in 2. was judged to have been reached, a time period that went back from the time $t_{k,j,N}$ when $N_k$ in 2. was reached $(t_{k,j,N}-N_k \Delta t)$ [$\Delta t$ is data obtainment time interval (measurement decomposition ability of apparatus)] is $t_{k,on}$.

4. Calculation of Difference $\Delta t_{1,k}$ in Reaction Start Time:

Using the value of reaction start time $t_{k,on}$ of each sensor det k determined in 3., a difference in the reaction start time $(\Delta t_{1,k}=t_{k,on}-t_{1,on})$ from the $t_{1,on}$ value of the first sensor det 1 is calculated.

5. Determination of Gas Type, Mixed Gas Component Ratio and the Like:

The gas type, mixed gas component ratio and the like can be determined by comparing the value of $\Delta t_{1,k}$ with the data obtained previously.

Figure 28:
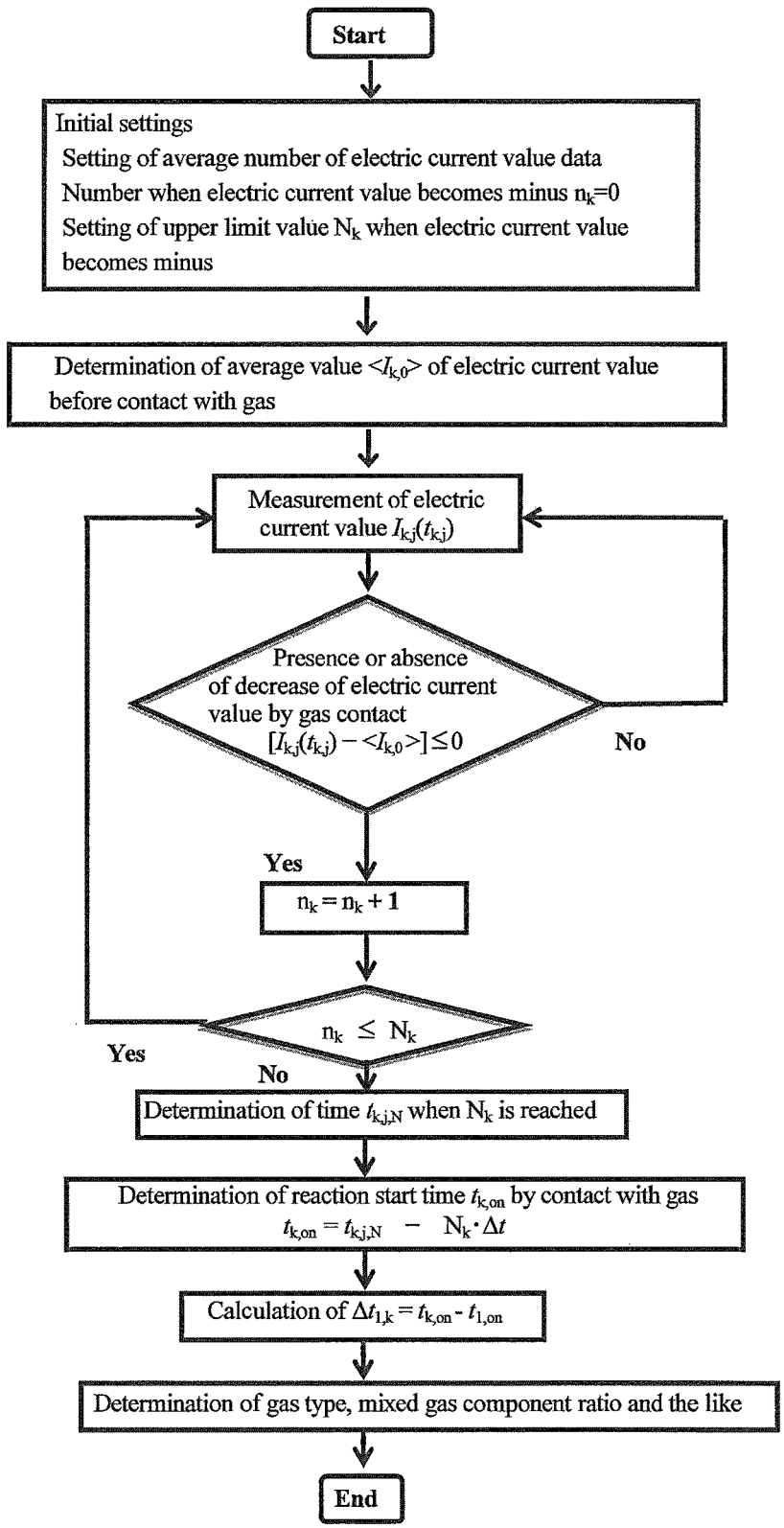
FIG. 28 is a flow chart showing an exemplary program relating to the determination of reaction start time of each sensor and the measurement of gas type, mixed gas component ratio and the like in the automatic gas analysis system using the gas sensor array of the present invention.

A flow chart is shown in FIG. 28.

[II] Measurement of Sensor Response S

The determination of the gas type can be performed more accurately by, for example, combining a program for determination by automatic measurement of sensor response S by the simple type sensor described in JP-B-5120904 by the present inventors. The following shows the program thereof. For the measurement, the first gas sensor (det 1) of a gas sensor array is used. In the following program, the measurement was performed at each sensor of a gas sensor.

1. Determination of Initial Electric Current Value $I_0$ Before Contact with Gas:

To reduce time variation due to the noise of the electric current that flows in the kth sensor det k before contact with a gas, an average time $<I_{k,0}>$ of the electric current value that flows in the sensor is determined.

2. Determination of the Presence or Absence of Decrease in Electric Current Value Due to Contact with Gas:

The kth sensor det k reacts on contact with a gas, and the electric current value $I_k$ that flows in this sensor starts to decrease from $<I_{k,0}>$. At this time, the data of the electric current value $I_{k,j}(t_{k,j})$ at a measurement time $t_{k,j}$ is obtained by performing an average treatment at a predetermined time interval. A difference in the electric current value between measurement times $t_{k,j}$ and $t_{k,j+1}$, $\Delta I_{k,j,J+1} = <I_{k,J+1}(t_{k,j+1})> - <I_{k,j}(t_{k,j})>$, is calculated, and plus and minus is determined.

3. Determination of Minimum Value of Electric Current Value of the Kth Sensor Det k Due to Contact with Gas:

The electric current value $<I_{k,m}(t_{k,m})>$ at the time $t_{k,m}$ when the electric current value of the kth sensor det k changes from minus to plus by the determination in 2. is the minimum value.

4. Calculation of Sensor Response:

The sensor response S of the kth sensor det k can be obtained by $[<I_{k,0}> - <I_{k,m}(t_{k,m})>]/<I_{k,0}>$.

5. Determination of Gas Type:

The gas type can be determined by comparing the S value with the data obtained previously.

Figure 29:
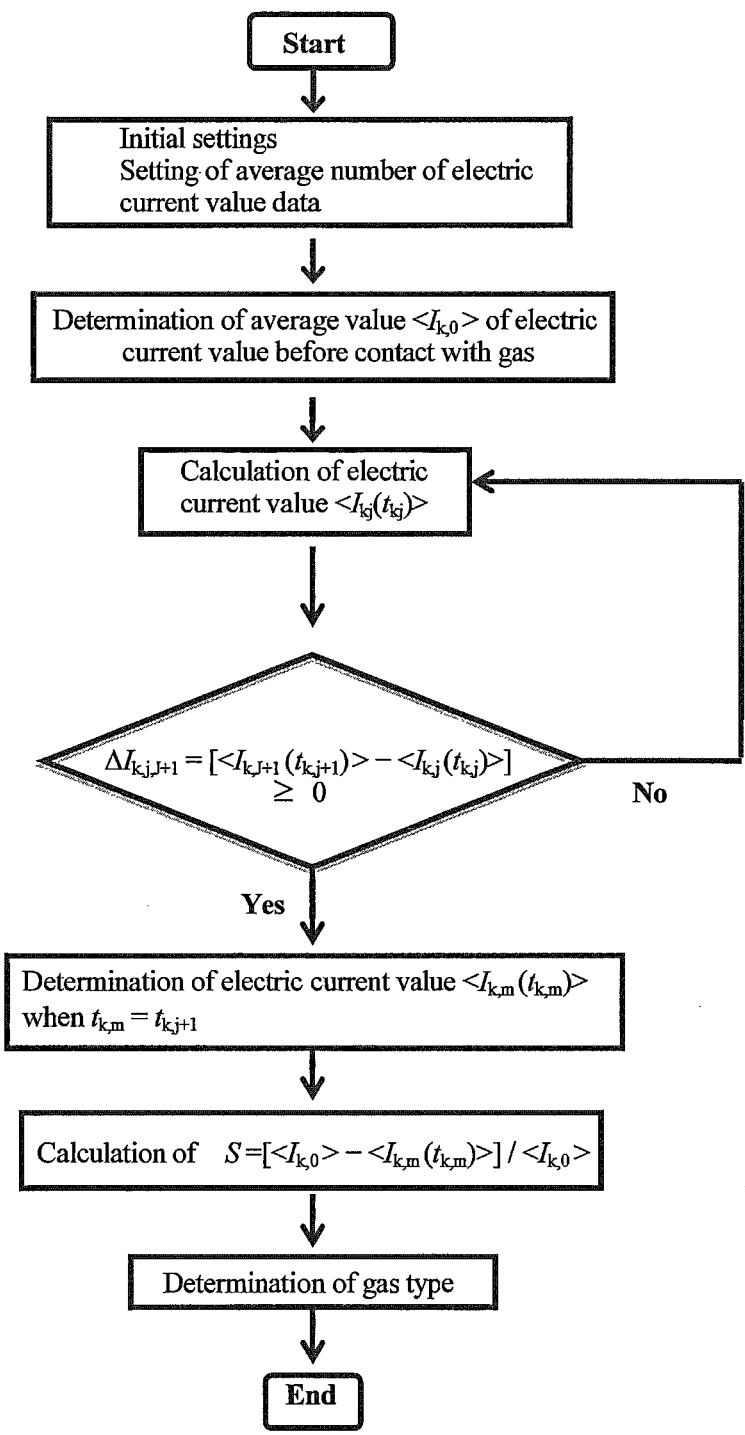
FIG. 29 is a flow chart showing an exemplary program relating to the measurement of sensor response S in the automatic gas analysis system using the gas sensor array of the present invention.

A flow chart is shown in FIG. 29.

EXAMPLES

The present invention is explained in more detail in the following by referring to Examples, which are not to be construed as limitative.

Example 1

Semiconductor Microcrystal

As semiconductor microcrystal, selenium nanowire was prepared. The selenium nanowire was prepared by the following method.

Commercially available granular amorphous selenium (purity: 99.9999%, Rare Metallic Co., Ltd.) was milled into a fine powder in a mortar. The granulated amorphous selenium was amorphous particle having a particle size of 20-30 μm. The finely divided powder of amorphous selenium (512 mg) was cast into ethanol (1 mL) in a glass tube, and the mixture was left standing at room temperature for 9 days. Ethanol was evaporated, and the residue was air-dried to give selenium nanowire. The size of the selenium nanowire was about 280 nm in diameter and about 2.6 μm in length. WO 2011/055751 (patent document 1) by the applicant of the present application can be referred to as for the adjustment of the shape and size of microcrystalline selenium.

<Gas Sensor Array>

On one surface of a copper-clad laminate (insulating layer: glass epoxy) using a copper foil having a thickness of 35 μm was formed a band-like lower electrode (width 1 mm×length 8.9 mm) (copper foil pattern), and on the both sides of the band-like electrode (copper foil pattern) were each formed a bottom part (width 0.8 mm×length 8.9 mm×depth 0.036 mm) of a groove for a gas flow path.

Next, on the band-like electrode (copper foil pattern) was adhered a double-sided adhesive carbon tape (width 1 mm×length 7 mm) (two-sided carbon adhesive tape manufactured by Nisshin EM Corporation, thickness 0.12 mm), and selenium nanowire (about 90 μg) was further applied thereonto to form a selenium nanowire accumulation layer (thickness 21 μm).

The copper foil of one surface of the copper-clad laminate (insulating layer: glass epoxy) using the copper foil (thickness 35 μm) was patterned to arrange 15 needle-like upper electrodes (copper foil pattern having width 0.21 mm×length 1 mm) at 0.21 mm intervals.

The first plate having the lower electrode formed from the above-mentioned copper-clad laminate and the accumulation layer of selenium nanowire, and the second plate having an upper electrode formed from the above-mentioned copper-clad laminate were placed with electrode-formed surfaces facing each other, and adhered with a trace amount of power such that the upper electrode was in good contact with the accumulation layer of selenium nanowire to produce a gas sensor array having the constitution shown in FIG. 1. The insulating layer derived from the copper-clad laminate in the first plate corresponds to substrate 8 in FIG. 1, and the insulating layer derived from the copper-clad laminate in the second plate corresponds to cover 10 in FIG. 1. The shape of the section orthogonal to the axis of a gas flow path was each width 0.8 mm×height 0.13 mm (cross-sectional area 0.104 mm$^2$). The double-sided carbon adhesive tape is compressed by adhesion of the first plate and second plate, and the thickness is considered to have decreased by about 35-50% from that before adhesion.

The gas sensor nearest to the gas introduction port of the gas sensor array was set to be the first gas sensor (det 1), and the remaining 15 gas sensors were numbered in the order of an increasing clearance from the first gas sensor (det 1). The electric current value of every gas sensor (any i$^{th}$ gas sensor (det i)) was measured under a constant voltage (5V) by a GPIB (General Purpose Interface Bus)-controlled digital multi meter (ADCMT 7461A), and the measurement data was constituted to be incorporated into a personal computer. GPIB control used was formed by a LabVIEW software manufactured by National Instrument. The minimum time decomposition ability was 0.05 sec.

Data analysis was performed by Excell or Igor software.

For gas development, an organic solvent was dropped onto a cotton swab (5 mmφ, length 10 mm), and the tip of this cotton swab was set at 1 mm from the gas sensor located most closely (the first gas sensor) to the gas introduction port into the gas flow path of the gas sensor array produced in the above-mentioned Example.

For gas flow measurement, an organic solvent was injected with a syringe into a Tedlar Bag, diluted by injecting air, extracted from the bag by using a mini pump (MP-Σ30N manufactured by SHIBATA SCIENTIFIC TECHNOLOGY LTD.), and blown at an optional flow rate from 1 mm from a gas sensor located most closely (the first gas sensor) to the gas introduction port into the gas flow path of the gas sensor array produced in the above-mentioned Example.

Experimental Example 1

1-Propanol was dropped onto a cotton swab (5 mmφ, length 10 mm), the tip of this cotton swab was set at 1 mm from the gas sensor located most closely (the first gas sensor) to the gas introduction port into the gas flow path of the gas sensor array produced in the above-mentioned Example. The gas volatilized from the cotton swab was flown from the gas introduction port 2A in the gas flow path 2 and the time-change spectra of electric current change of the first gas sensor (det 1), the fifth gas sensor (det 5), the ninth gas sensor (det 9) and the thirteenth gas sensor (det 13) were measured. The results thereof are shown in FIG. 7(A) and FIG. 7(B).

Experimental Example 2

Methanol was dropped onto a cotton swab instead of 1-propanol and, in the same manner as in Experimental Example 1, the gas volatilized from the cotton swab was flown in the gas flow path of the gas sensor array, and the time-change spectra of electric current change of the first gas sensor (det 1), the fifth gas sensor (det 5), the ninth gas sensor (det 9), the 11th gas sensor (det 11) and the thirteenth gas sensor (det 13) were measured. The results thereof are shown in FIG. 8(A) and FIG. 8(B).

Experimental Example 3

1-Octanol was dropped onto a cotton swab instead of 1-propanol and, in the same manner as in Experimental Example 1, the gas volatilized from the cotton swab was flown in the gas flow path of the gas sensor array, and the time-change spectra of electric current change of the first gas sensor (det 1), the second gas sensor (det 2), the third gas sensor (det 3) and the ninth gas sensor (det 9) were measured. The results thereof are shown in FIG. 10(A) and FIG. 10(B).

Experimental Example 4

(1) A mixture of acetone (300 mL) and toluene (60 mL), (2) a mixture of acetone (300 mL) and toluene (120 mL), and (3) a mixture of acetone (300 mL) and toluene (240 mL) were respectively prepared. In addition, (4) acetone (300 mL) and (5) toluene (300 mL) were prepared. As for each of such 5 kinds, in the same manner as in Experimental Example 1, the volatilized gas was flown in the gas flow path of the gas sensor array, and the time-change spectra of electric current change of the first gas sensor (det 1), the fifth gas sensor (det 5), the ninth gas sensor (det 9) and the thirteenth gas sensor (det 13) were measured. The results of the time-change spectrum of electric current change of the mixture of (1) are shown in FIG. 12(A) and FIG. 12(B).

Experimental Example 5

(1) A mixture of acetone (300 mL) and benzene (60 mL), (2) a mixture of acetone (300 mL) and benzene (120 mL), and (3) a mixture of acetone (300 mL) and benzene (240 mL) were respectively prepared. As for each of these 3 kinds, in the same manner as in Experimental Example 1, the volatilized gas was flown in the gas flow path of the gas sensor array, and the time-change spectra of electric current change of the first gas sensor (det 1), the fifth gas sensor (det 5) and the ninth gas sensor (det 9) were measured. The results thereof are shown in FIG. 13(A). FIG. 13(B) shows the relationship between the ratio of benzene in the mixture (mixed gas), and the peak arrival time in the time-change spectrum of electric current change of the first gas sensor (det 1), the ninth gas sensor (det 9) and the thirteenth gas sensor (det 13).

Experimental Example 6

In the same manner as in Experimental Example 1, the gas volatilized from the mixture of acetone (300 mL) and benzene (240 mL) was flown in the gas flow path of the gas sensor array for 7.0 sec, and the time-change spectra of electric current change of the first gas sensor (det 1) and the thirteenth gas sensor (det 13) were measured. The results thereof are shown in FIG. 14(A). In the same manner as in Experimental Example 1, the gas volatilized from the mixture of acetone (300 mL) and benzene (240 mL) was flown in the gas flow path of the gas sensor array for 74.0 sec, and the time-change spectra of electric current change of the first gas sensor (det 1) and the thirteenth gas sensor (det 13) were measured. The results thereof are shown in FIG. 14(B). The inserted figure in FIG. 14(B) is a view wherein a gas introduction start time (40 sec-80 sec from the start of test) into the gas flow path in FIG. 14(B) is the horizontal axis.

Experimental Example 7

(1) A mixture of 1-butanol (60 mL) and 1-octanol (240 mL), (2) a mixture of 1-butanol (120 mL) and 1-octanol (240 mL), and (3) a mixture of 1-butanol (240 mL) and 1-octanol (240 mL) were respectively prepared. As for each of these two kinds, in the same manner as in Experimental Example 1, the volatilized gas was flown in the gas flow path of the gas sensor array, and the time-change spectra of electric current change of the first gas sensor (det 1), the second gas sensor (det 2), the third gas sensor (det 3), the fourth gas sensor (det 4) and the ninth gas sensor (det 9) were measured. In the results, the time-change spectra of electric current change of the first gas sensor (det 1), the third gas sensor (det 3) and the ninth gas sensor (det 9) of the mixture of (2) and (3), and 1-octanol alone are shown in FIG. 17(A)-FIG. 17(C). FIG. 18 shows the relationship between the delay time in the time-change spectra of electric current change of the first gas sensor (det 1), the second gas sensor (det 2), the third gas sensor (det 3), the fourth gas sensor (det 4) and the ninth gas sensor (det 9) from the gas reaction start time of the first gas sensor, and a mixed gas of 1-butanol and 1-octanol.

Experimental Example 8

Ethanol gas (0.5 mL) diluted with air (5 L) was prepared. This ethanol gas was flown into the gas introduction port of the gas sensor array produced in the above-mentioned Example at flow rates of 0.1 L/min, 0.2 L/min, 0.3 L/min, 0.4 L/min, 0.5 L/min, 2.0 L/min and 3.0 L/min, and the delay time in the time-change spectra of electric current change between the first gas sensor (det 1) and the ninth gas sensor (det 9) was measured. The results thereof are shown in FIG. 19.

Experimental Example 9

Ethanol (0.08 mL, 0.1 mL, 0.15 mL, 0.25 mL, 0.5 mL, 0.75 mL) was diluted with air (5 L) to give ethanol gas having a concentration of 6750 ppm, 8440 ppm, 12660 ppm, 21110 ppm, 42210 ppm, 63320 ppm. These gases were flown into the gas introduction port of the gas sensor array produced in the above-mentioned Example at a flow rate of 0.2 L/min, and the delay time in the time-change spectra of electric current change between the first gas sensor (det 1) and the thirteenth gas sensor (det 13) was measured. The results thereof are shown in FIG. 20.

Experimental Example 10

Carbon dioxide gas (100%) as an inorganic gas was blown in the gas flow path of gas sensor array 1 of the example of FIG. 1 from the gas introduction port of the gas sensor array at a flow rate of 0.2 mL/min, and the delay time in the time-change spectra of electric current change of the first gas sensor (det 1), the second gas sensor (det 2), the third gas sensor (det 3) and the fourth gas sensor (det 4), counting from the gas introduction port 2A of the gas flow path 2 was measured. The results thereof are shown in FIG. 21(A) and FIG. 21(B).

Experimental Example 11

As a gas sensor array, the gas sensor array used in Experimental Example 1, which was gold-plated on the surface of the copper foil pattern of the upper and lower electrodes, was prepared.

(1) An acetone (300 mL) solution, (2) a mixture of acetone (300 mL) and benzene (60 mL), (3) a mixture of acetone (300 mL) and benzene (120 mL), (4) a mixture of acetone (300 mL) and benzene (240 mL), (5) a mixture of acetone (300 mL) and benzene (300 mL), (6) a mixture of acetone (240 mL) and benzene (300 mL), (7) a mixture of acetone (120 mL) and benzene (300 mL), (8) a mixture of acetone (60 mL) and benzene (300 mL), and (9) a benzene (300 mL) solution were respectively prepared. In the same manner as in Experimental Example 1, a volatilization gas was flown in the gas flow path of the gas sensor array, and the time-change spectra of electric current change of the first gas sensor (det 1) and the thirteenth gas sensor (det 13) were measured. The time-change spectrum of electric current change when the component ratio of a mixed gas (acetone/benzene) is 0.29/0.71 is shown in FIG. 15(A), and FIG. 15(B) is an enlarged view when 20 sec-70 sec passed from the start of the measurement. FIG. 16 shows the relationship between the component ratio of the thus-obtained mixed gas of benzene and acetone, and a difference in the delay time ($\Delta t_{1,13}$) between the first gas sensor (det 1) and the thirteenth gas sensor (det 13). The delay time difference ($\Delta t_{1,13}$) is a difference between the time when the electric current starts to decrease upon contact with a gas in the first gas sensor (det 1) (reaction start time) and the time when the electric current starts to decrease upon contact with a gas in the thirteenth gas sensor (det 13) (reaction start time).

INDUSTRIAL APPLICABILITY

According to the present invention, a gas sensor array which is compact, can operate at room temperature, can specify gas type, and can analyze mixed gas components can be provided. Since the gas sensor array of the present invention can specify gas type, analyze mixed gas components, and can afford analysis results in a short time, environmental monitoring at the site, loading on robots, utilization in the medical field and the like can be expected.

EXPLANATION OF SYMBOLS

1, 50, 51, 52, 53 gas sensor array
2 gas flow path
2A gas introduction port
2B gas discharge port
3 gas sensor
4 first electrode
5 second electrode
6 semiconductor microcrystal
6A accumulation layer of semiconductor crystal
7 laminate
8 substrate
9 conductive double-sided tape
10 cover
11A, 11B insulating wall
12 lead wire
13 electric current meter
14 power source
G gas to be analyzed

The invention claimed is:

1. A gas sensor array comprising a gas flow path in which a gas to be analyzed flows, and
a plurality of gas sensors set along a gas flowing direction of the gas flow path comprising a single first electrode, a plurality of second electrodes, and semiconductor microcrystals that come into contact with the gas to be analyzed that are disposed between the single first electrode and the plurality of second electrodes, wherein each gas sensor is composed of:
(i) a laminate wherein an accumulation layer of the semiconductor microcrystals is formed on the single first electrode,
(ii) the gas flow path is configured on the side of the laminate to be in contact with the accumulation layer of the semiconductor microcrystals, and
(iii) the plurality of second electrodes are provided side by side on the accumulation layer of the semiconductor crystals, along the gas flowing direction of the gas flow path.

2. The gas sensor array according to claim 1, wherein the laminate is a band-like laminate with the accumulation layer of the semiconductor crystals being formed on the single first electrode in a band-like flat shape,
the gas flow path is configured at least on one side of the transverse direction of the band-like laminate and along the longitudinal direction of the band-like laminate, and
the second electrodes are each configured such that the axis thereof is approximately orthogonal to the longitudinal direction of the band-like laminate.

3. The sensor array according to claim 2, wherein a conducting layer is laminated on the surface of the single first electrode, and the semiconductor crystals are formed on the accumulation layer of the conducting layer.

4. The sensor array according to claim 2, wherein the semiconductor microcrystal is microcrystalline selenium.

5. The sensor array according to claim 4, wherein the microcrystalline selenium is a selenium nanowire.

6. The sensor array according to claim 2, wherein the gas to be analyzed that flows in the gas flow path comes into contact with the semiconductor microcrystals of the plurality of gas sensors under a constant voltage and a delay time between different sensors in a time-change spectrum of electric current change that occurs in each gas sensor is detected.

7. The sensor array according to claim 1, wherein a conducting layer is laminated on the surface of the single first electrode, and the semiconductor crystals are formed on the accumulation layer of the conducting layer.

8. The sensor array according to claim 1, wherein the single first electrode has a surface made of gold or silver.

9. The sensor array according to claim 1, wherein the semiconductor microcrystal is microcrystalline selenium.

10. The sensor array according to claim 9, wherein the microcrystalline selenium is a selenium nanowire.

11. The sensor array according to claim 1, wherein the gas to be analyzed that flows in the gas flow path comes into contact with the semiconductor microcrystals of the plurality of gas sensors under a constant voltage and a delay time between different sensors in a time-change spectrum of electric current change that occurs in each gas sensor is detected.

12. The sensor array according to claim 11, wherein the delay time is a delay time in the start of a reaction of the time-change spectrum.

13. The gas sensor array according to claim 1, wherein the gas to be analyzed that flows in the gas flow path comes into contact with the semiconductor microcrystals of the plurality of gas sensors under a constant voltage and a difference in the shape of a time-change spectrum of electric current change between different sensors is detected.

14. The gas sensor array according to claim 1, which is for an organic gas.

15. A method of analyzing a gas, comprising flowing a gas to be analyzed in the gas flow path while applying a constant voltage to the plurality of gas sensors in the gas sensor array according to claim 1, and specifying the gas type of the gas to be analyzed based on a delay time between different sensors in a time-change spectrum of electric current change that occurs in each of the plurality of gas sensors.

16. A method of analyzing a gas, comprising flowing a gas to be analyzed in the gas flow path while applying a constant voltage to the plurality of gas sensors in the gas sensor array according to claim 1, and specifying a component ratio of the gas to be analyzed based on a delay time between different sensors in a time-change spectrum of electric current change that occurs in each of the plurality of gas of sensors.

17. A method of analyzing a gas, comprising flowing a gas to be analyzed in the gas flow path while applying a constant voltage to the plurality of gas sensors in the gas sensor array according to claim 1, and specifying a component ratio of the gas to be analyzed from comparison of a peak arrival time between different sensors in a time-change spectrum of electric current change that occurs in each of the plurality of gas sensors.

18. A method of analyzing a gas, comprising flowing a gas to be analyzed in the gas flow path under plural conditions with varying flowing time of a gas to be analyzed in the gas flow path while applying a constant voltage to the plurality of gas sensors in the gas sensor array according to claim 1, observing time-change spectra of electric current change occurring in plural gas sensors under respective conditions, and specifying gas components of the gas to be analyzed, which is composed of a mixed gas, by comparison of the time-change spectra obtained under the plural conditions.

19. A gas analysis system comprising the gas sensor array according to claim 1, and a calculation part for specifying a gas type, specifying a component ratio of a mixed gas or specifying a gas component of a mixed gas, based on an electric output value based on a time-change spectrum of electric current change that occurs in each gas sensor when a gas to be analyzed is flown in the gas flow path while applying a constant voltage to the plurality of gas sensors in the gas sensor array, and comparison results with numerical values preserved in a database.

* * * * *